United States Patent
Klempner et al.

(10) Patent No.: US 11,827,670 B2
(45) Date of Patent: Nov. 28, 2023

(54) ANTI-CFAE ANTIBODIES AND METHODS OF USE

(71) Applicant: University of Massachusetts, Boston, MA (US)

(72) Inventors: Mark S. J. Klempner, Boston, MA (US); Yang Wang, Wellesley, MA (US); Serena Giuntini, Belmont, MA (US)

(73) Assignee: University of Massachusetts, Boston, MA (US)

( * ) Notice: Subject to any disclaimer, the term of this patent is extended or adjusted under 35 U.S.C. 154(b) by 201 days.

(21) Appl. No.: 17/292,078

(22) PCT Filed: Nov. 12, 2019

(86) PCT No.: PCT/US2019/061026
§ 371 (c)(1),
(2) Date: May 7, 2021

(87) PCT Pub. No.: WO2020/097627
PCT Pub. Date: May 14, 2020

(65) Prior Publication Data
US 2021/0388068 A1  Dec. 16, 2021

Related U.S. Application Data

(60) Provisional application No. 62/758,114, filed on Nov. 9, 2018.

(51) Int. Cl.
*C07K 16/12* (2006.01)
*A61P 31/04* (2006.01)
*A61K 39/00* (2006.01)

(52) U.S. Cl.
CPC .......... *C07K 16/1232* (2013.01); *A61P 31/04* (2018.01); *A61K 2039/505* (2013.01); *A61K 2039/545* (2013.01); *C07K 2317/21* (2013.01); *C07K 2317/34* (2013.01); *C07K 2317/92* (2013.01)

(58) Field of Classification Search
None
See application file for complete search history.

(56) References Cited

U.S. PATENT DOCUMENTS

| 2004/0170630 A1 | 9/2004 | Huang et al. |
| 2007/0280945 A1 | 12/2007 | Stevens et al. |
| 2016/0304622 A1 | 10/2016 | Miyakoshi et al. |

FOREIGN PATENT DOCUMENTS

| WO | WO-2018/080812 A1 | 5/2018 |
| WO | WO-2018/119425 A2 | 6/2018 |

OTHER PUBLICATIONS

Extended European Search Report for European Patent Application No. 19882282.7, dated Nov. 9, 2022 (11 pages).
Partial Supplementary European Search Report for European Application No. 19882282.7, dated Aug. 8, 2022 (13 pages).
Savarino et al., "Prophylactic Efficacy of Hyperimmune Bovine Colostral Antiadhesin Antibodies Against Enterotoxigenic *Escherichia coli* Diarrhea: A Randomized, Double-Blind, Placebo-Controlled, Phase 1 Trial," J Infect Dis. 216(1):7-13 (Jul. 1, 2017).
Stoppato et al., "Oral administration of an anti-CfaE secretory IgA antibody protects against Enterotoxigenic *Escherichia coli* diarrheal disease in a nonhuman primate model," Vaccine. 38(10):2333-2339 (Jan. 31, 2020) (7 pages).
Giuntini et al., "Identification and Characterization of Human Monoclonal Antibodies for Immunoprophylaxis Against Enterotoxigenic *Escherichia coli* Infection," Infect Immun. 86(8):e00355-18 (includes supplemental content) (2018) (12 pages).
International Preliminary Report on Patentability for International Application No. PCT/US2019/061026, dated May 11, 2021 (8 pages).
International Search Report and Written Opinion for International Application No. PCT/US2019/061026, dated Mar. 24, 2020 (18 pages).
Invitation to Pay Additional Fees for International Application No. PCT/US2019/061026, dated Jan. 31, 2020 (2 pages).

*Primary Examiner* — Jana A Hines
*Assistant Examiner* — Khatol S Shahnan Shah
(74) *Attorney, Agent, or Firm* — Clark & Elbing LLP

(57) ABSTRACT

The invention provides anti-CfaE antibodies and methods of using the same.

11 Claims, 9 Drawing Sheets

Specification includes a Sequence Listing.

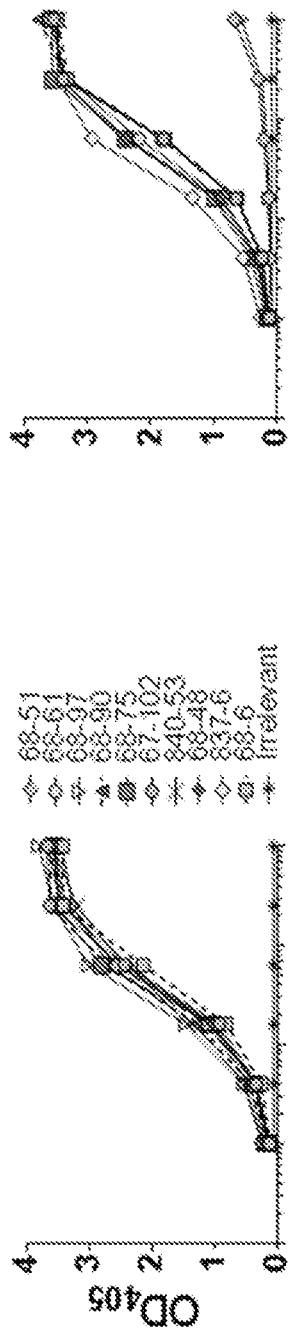
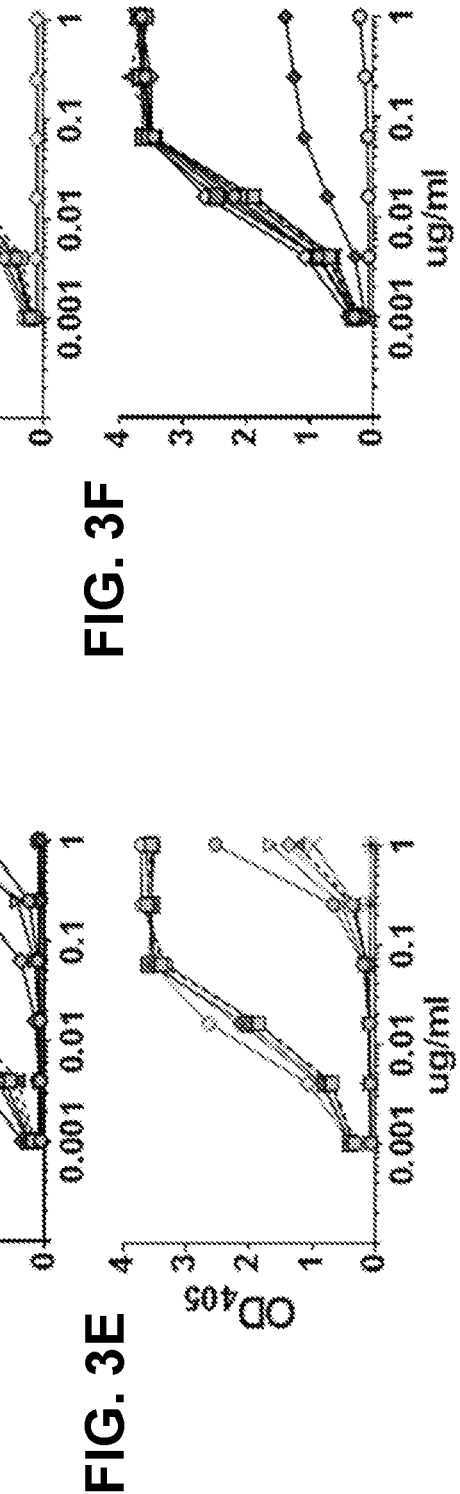
FIG. 3A  FIG. 3B  FIG. 3C  FIG. 3D  FIG. 3E  FIG. 3F

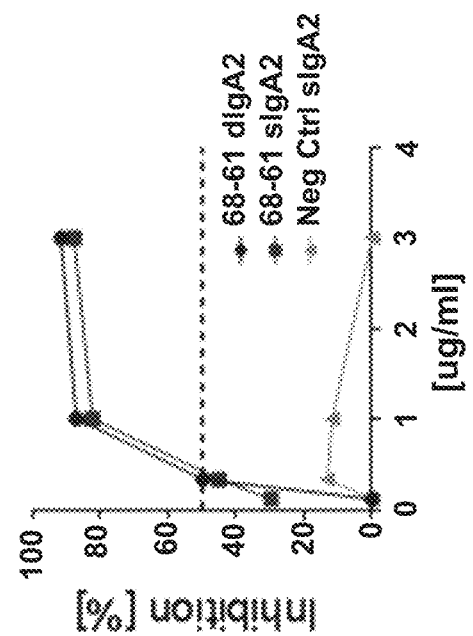
FIG. 8C
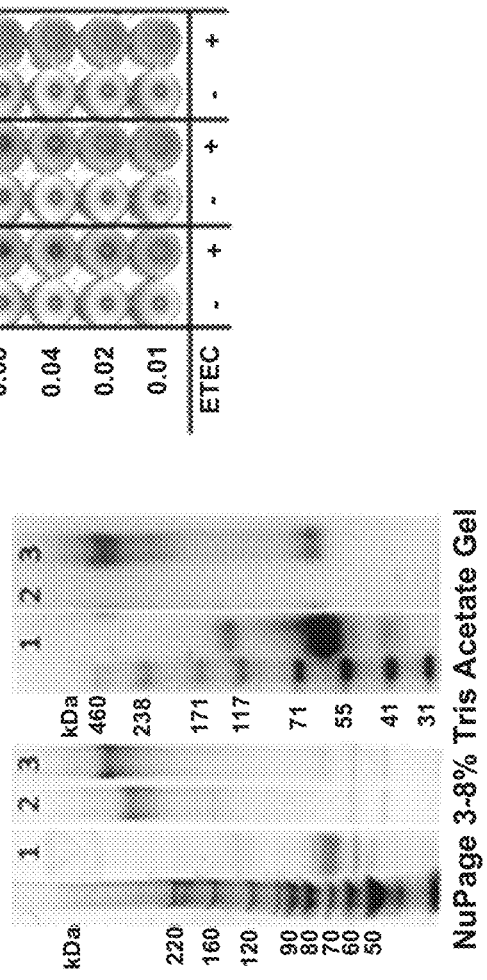
FIG. 8B
FIG. 8A

US 11,827,670 B2

ANTI-CFAE ANTIBODIES AND METHODS OF USE

STATEMENT AS TO FEDERALLY FUNDED RESEARCH

This invention was made with government support under Grant No. DARPA-BAA-13-03 awarded by the Department of Defense. The government has certain rights in the invention.

SEQUENCE LISTING

The instant application contains a Sequence Listing which has been submitted electronically in ASCII format and is hereby incorporated by reference in its entirety. Said ASCII copy, created on Nov. 12, 2019, is named 50811-008WO2—Sequence Listing_ST25 and is 17,536 bytes in size.

BACKGROUND OF THE INVENTION

Enterotoxigenic *Escherichia coli*(ETEC) is one of the main causes of diarrhea in infants in the developing world, as well as the major cause of traveler's diarrhea. Transmission of ETEC occurs when contaminated food or water is ingested. ETEC infections are characterized by diarrhea, vomiting, stomach cramps, and in some cases mild fever. Symptoms usually occur 1-3 days after infection and last for a few days. When adult travelers develop ETEC-related diarrhea, a short course of antibiotics can decrease the duration and volume of diarrhea. However, ETEC strains are becoming increasingly resistant to antibiotics, and there are currently no licensed vaccines for protecting travelers against ETEC-related diarrhea. Accordingly, there exists a need for improved treatments or prevention of ETEC-related disorders.

SUMMARY OF THE INVENTION

The invention provides anti-colonization factor antigen I adhesin subunit E (CfaE) antibodies and methods of their use.

In one aspect, the invention features an isolated antibody that specifically binds colonization factor antigen I adhesin subunit E (CfaE), wherein the antibody includes the following complementarity determining regions (CDRs): (a) a CDR-H1 including the amino acid sequence of GGTFSSFAIS (SEQ ID NO: 1); (b) a CDR-H2 including the amino acid sequence of RIIPILDIVKYAQRFQG (SEQ ID NO: 2); (c) a CDR-H3 including the amino acid sequence of ARDDIAGSDFDI (SEQ ID NO: 3); (d) a CDR-L1 including the amino acid sequence of QGISSW (SEQ ID NO: 4); (e) a CDR-L2 including the amino acid sequence of AAS (SEQ ID NO: 5); and (f) a CDR-L3 including the amino acid sequence of QQYTSYPYT (SEQ ID NO: 6), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6, and/or (ii) one, two, or three amino acid substitutions relative to the amino acid sequence of any one of SEQ ID NOs: 1-6.

In some embodiments, the antibody further includes the following heavy chain framework regions (FRs): (a) an FR-H1 including the amino acid sequence of QVQLVQS-GAEVKNPGSSVRVSCEAS (SEQ ID NO: 7); (b) an FR-H2 including the amino acid sequence of WVRQAPGQ-GLEWMG (SEQ ID NO: 8); (c) an FR-H3 including the amino acid sequence of RVTISADKST-STAYMELSSLRSEGTAVYYC (SEQ ID NO: 9); and (d) an FR-H4 including the amino acid sequence of WGQGTMVTVSSAST (SEQ ID NO: 10), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 7-10.

In some embodiments, the antibody further includes the following light chain FRs: (a) an FR-L1 including the amino acid sequence of DIQMTQSPSSLSASVGDRVTITCRAS (SEQ ID NO: 11); (b) an FR-L2 including the amino acid sequence of LAWYQQKPEKAPKSLIY (SEQ ID NO: 12); (c) an FR-L3 including the amino acid sequence of SLQSGVPSRFSGSGSGTDFTLTISSLQPEDFATYYC (SEQ ID NO: 13); and (d) an FR-L4 including the amino acid sequence of FGQGTKLEIK (SEQ ID NO: 14), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 11-14.

In some embodiments, the antibody includes a heavy chain variable (VH) domain including an amino acid sequence having at least 95%, at least 96%, at least 97%, at least 98%, or at least 99% sequence identity to the amino acid sequence of SEQ ID NO: 15 and a light chain variable (VL) domain including an amino acid sequence having at least 95%, at least 96%, at least 97%, at least 98%, or at least 99% sequence identity to the amino acid sequence of SEQ ID NO: 16.

In another aspect, the invention features an isolated antibody that specifically binds CfaE including a VH domain of SEQ ID NO: 15 and a VL domain of SEQ ID NO: 16.

In another aspect, the invention features an isolated antibody that specifically binds CfaE, wherein the antibody includes the following CDRs: (a) a CDR-H1 including the amino acid sequence of GGSFSGYSWS (SEQ ID NO: 17); (b) a CDR-H2 including the amino acid sequence of EIYHSGSTNYNPSLKS (SEQ ID NO: 18); (c) a CDR-H3 including the amino acid sequence of ARENLQGYYYYGMDV (SEQ ID NO: 19); (d) a CDR-L1 including the amino acid sequence of QGISSS (SEQ ID NO: 20); (e) a CDR-L2 including the amino acid sequence of DAS (SEQ ID NO: 21); and (f) a CDR-L3 including the amino acid sequence of QQFNSYPRT (SEQ ID NO: 22), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 17-22, and/or (ii) one, two, or three amino acid substitutions relative to the amino acid sequence of any one of SEQ ID NOs: 17-22.

In some embodiments, the antibody further includes the following heavy chain FRs: (a) an FR-H1 including the amino acid sequence of QVQLQQWGAGLLKPSETLSLT-CAVY (SEQ ID NO: 23); (b) an FR-H2 including the amino acid sequence of WIRQSPGKGLEWIG (SEQ ID NO: 24); (c) an FR-H3 including the amino acid sequence of RVTIS-GDTSKNQFSLKLSSVTAADTAVYYC (SEQ ID NO: 25); and (d) an FR-H4 including the amino acid sequence of WGQGTTVTVSSAST (SEQ ID NO: 26), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 23-26.

In some embodiments, the antibody further includes the following light chain FRs: (a) an FR-L1 including the amino acid sequence of AIQLTQSPSSLSASVGDRVTITCRAS (SEQ ID NO: 27); (b) an FR-L2 including the amino acid sequence of LAWYQQKPGKAPKLLIY (SEQ ID NO: 28); (c) an FR-L3 including the amino acid sequence of SLESGVPSRFSGSGSGTDFTLTISSLQPEDFATYYC (SEQ ID NO: 29); and (d) an FR-L4 including the amino acid sequence of FGQGTKVEIK (SEQ ID NO: 30), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 27-30.

In some embodiments, the antibody includes a VH domain including an amino acid sequence having at least 95%, at least 96%, at least 97%, at least 98%, or at least 99% sequence identity to the amino acid sequence of SEQ ID NO: 31 and a VL domain including an amino acid sequence having at least 95%, at least 96%, at least 97%, at least 98%, or at least 99% sequence identity to the amino acid sequence of SEQ ID NO: 32.

In another aspect, the invention features an isolated antibody that specifically binds CfaE including a VH domain of SEQ ID NO: 31 and a VL domain of SEQ ID NO: 32.

In another aspect, the invention features an isolated antibody that specifically binds CfaE, wherein the antibody includes the following CDRs: (a) a CDR-H1 including the amino acid sequence of GGSFSAYYWS (SEQ ID NO: 33); (b) a CDR-H2 including the amino acid sequence of EINHSGNTNYNPSLES (SEQ ID NO: 34); (c) a CDR-H3 including the amino acid sequence of ARNWGPNAFDI (SEQ ID NO: 35); (d) a CDR-L1 including the amino acid sequence of QDITSW (SEQ ID NO: 36); (e) a CDR-L2 including the amino acid sequence of AAS (SEQ ID NO: 37); and (f) a CDR-L3 including the amino acid sequence of QQANIFPYT (SEQ ID NO: 38), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 33-38, and/or (ii) one, two, or three amino acid substitutions relative to the amino acid sequence of any one of SEQ ID NOs: 33-38.

In some embodiments, the antibody further includes the following heavy chain FRs: (a) an FR-H1 including the amino acid sequence of QVQLQQWGAGLLKPSETLSLT-CAVY (SEQ ID NO: 39); (b) an FR-H2 including the amino acid sequence of WIRQPPGKGLEWIG (SEQ ID NO: 40); (c) an FR-H3 including the amino acid sequence of RVTISVDTSKNQVSLKQSSVTAADTAVYYC (SEQ ID NO: 41); and (d) an FR-H4 including the amino acid sequence of WGRGTMVTVSSAST (SEQ ID NO: 42), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 39-42.

In some embodiments, the antibody further includes the following light chain FRs: (a) an FR-L1 including the amino acid sequence of DIQMTQSPSSVSASVGDRVTITCRAS (SEQ ID NO: 43); (b) an FR-L2 including the amino acid sequence of LVWYQHKPGKAPKLLIY (SEQ ID NO: 44); (c) an FR-L3 including the amino acid sequence of SLQSGVPSRFSGSGSGTDFTLTISSLQPEDFATYYC (SEQ ID NO: 45); and (d) an FR-L4 including the amino acid sequence of FGQGTKLEIK (SEQ ID NO: 46), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 43-46.

In some embodiments, the antibody includes a VH domain including an amino acid sequence having at least 95%, at least 96%, at least 97%, at least 98%, or at least 99% sequence identity to the amino acid sequence of SEQ ID NO: 47 and a VL domain including an amino acid sequence having at least 95%, at least 96%, at least 97%, at least 98%, or at least 99% sequence identity to the amino acid sequence of SEQ ID NO: 48.

In another aspect, the invention features an isolated antibody that specifically binds CfaE including a VH domain of SEQ ID NO: 47 and a VL domain of SEQ ID NO: 48.

In some embodiments of any of the preceding aspects, the antibody is a monoclonal antibody, a human antibody, an IgG class antibody (e.g., an IgG1 subclass antibody), and/or an IgA (e.g., an IgA1 or an IgA2 subclass antibody) class antibody (e.g., a secretory IgA (sIgA) or dimeric IgA (dIgA) class antibody).

In some embodiments, the antibody is a full-length antibody. In other embodiments, the antibody is an antibody fragment that specifically binds CfaE selected from the group consisting of Fab, Fab', Fab'-SH, Fv, single chain variable fragment (scFv), and (Fab')$_2$ fragments.

In some embodiments, the antibody is capable of inhibiting mannose-resistant hemagglutination of human group A erythrocytes with a maximal inhibitory concentration ($IC_{100}$) of between about 0.10 µg/mL and about 0.25 µg/mL. In some embodiments, the inhibiting is measured using a mannose-resistant hemagglutination (MRHA) assay.

In some embodiments, the antibody specifically binds CfaE expressed on the surface of a live enterotoxigenic *Escherichia coli* (ETEC) strain (e.g., a live H10407 ETEC strain) with a $K_D$ of between about 0.1 nM and about 10 nM (e.g., about 0.6 nM and about 1.2 nM). In some embodiments, the $K_D$ is determined by flow cytometry at 37° C.

In some embodiments, the antibody is capable of inhibiting the binding of ETEC bacteria to intestinal cells (e.g., Caco-2 human intestinal epithelial cells) with a 50% inhibitory concentration ($IC_{50}$) of between about 0.10 µg/mL and about 10 µg/mL (e.g., between about 0.30 µg/mL and about 1.3 µg/mL).

In some embodiments, the inhibiting is measured using a Caco-2 adhesion assay.

In another aspect, the invention features a composition, e.g., a pharmaceutical composition, including the antibody of any of the preceding aspects.

In some embodiments, the pharmaceutical composition further includes a pharmaceutically acceptable carrier, excipient, or diluent.

In some embodiments, the pharmaceutical composition is formulated for treating a disorder associated with an ETEC infection, e.g., ETEC-related diarrhea, in a subject.

In some embodiments, the pharmaceutical composition is formulated for oral administration including from 2% to 60% (w/v) (e.g., 2%, 5%, 10%, 15%, 20%, 25%, 30%, 35%, 40%, 45%, 50%, or 55% (w/v)) of the antibody.

In another aspect, the invention features an isolated nucleic acid encoding the antibody of any one of the preceding aspects.

In another aspect, the invention features a vector including the nucleic acid of the preceding aspect.

In another aspect, the invention features a host cell including the vector of the preceding aspect. In some embodiments, the host cell is a mammalian cell (e.g., a Chinese hamster ovary (CHO) cell) or a prokaryotic cell (e.g., an *E. coli* cell).

In another aspect, the invention features a method of producing an antibody that specifically binds CfaE, the method including culturing the host cell including the nucleic acid the preceding aspects in a culture medium. In some embodiments, the method further includes recovering the antibody from the host cell or the culture medium.

In another aspect, the invention features a method of treating a subject having a disorder associated with an ETEC infection including administering a therapeutically effective amount of the antibody or pharmaceutical composition of any of the preceding aspects, thereby treating the subject.

In another aspect, the invention features a method of treating a subject at risk of developing a disorder associated with an ETEC infection including administering a therapeutically effective amount of the antibody or the pharmaceutical composition of any of the preceding aspects, thereby treating the subject.

In some embodiments, the antibody is administered to the subject at a dosage of about 0.01 mg/kg to about 50 mg/kg (e.g., about 0.1 mg/kg to about 25 mg/kg, about 1 mg/kg to about 20 mg/kg, or about 10 mg/kg). In some embodiments, the subject is administered at least one dose of the antibody or the pharmaceutical composition. In further embodiments, the subject is administered at least two doses of the antibody or the pharmaceutical composition.

In some embodiments, the disorder associated with an ETEC infection is ETEC-related diarrhea.

In some embodiments, the antibody is administered orally to the subject.

In some embodiments, the antibody is administered subcutaneously to the subject.

In a final aspect, the invention features a kit including an isolated antibody that specifically binds colonization factor antigen I adhesin subunit E (CfaE) and a package insert including instructions for using the antibody for treating a subject having or at risk of developing a disorder associated with an ETEC infection.

The invention provides numerous advantages. For example, described herein are anti-CfaE human monoclonal antibodies capable of inhibiting ETEC adhesion to host intestinal cells. The antibodies can be administered orally, and can be used to treat ETEC-related disease (e.g., diarrhea). Furthermore, the anti-CfaE antibodies described herein also represent an effective strategy for immunoprophylaxis against ETEC.

Other features and advantages of the invention will be apparent from the following description of the preferred embodiments thereof, and from the claims.

BRIEF DESCRIPTION OF THE DRAWINGS

FIGS. 3A-3F are graphs showing binding of anti-CfaE antibodies to various mutants of recombinant CfaE as measured by ELISA. The binding of the antibodies was determined for wild-type CfaE (FIG. 3A), Arg67Ala mutant (FIG. 3B), Thr91Ala mutant (FIG. 3C), Arg145Ala mutant (FIG. 3D), Tyr183Ala mutant (FIG. 3E), and Asn127Ala mutant (FIG. 3F).

Figure 1A:
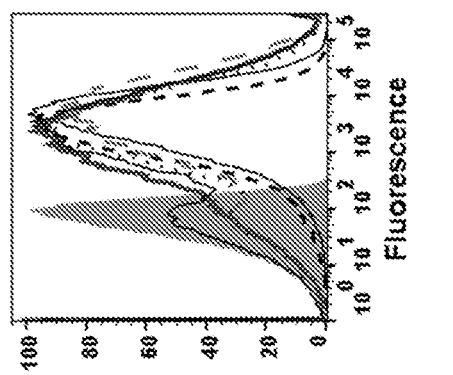
FIG. 1A is a graph showing concentration-dependent binding of anti-CfaE antibodies as measured by ELISA. IgG bound to immobilized recombinant CfaE-N was detected with an anti-human IgG Fc-chain-specific alkaline phosphatase-conjugated antibody. Error bars represent the range in OD values observed in two independent experiments. The binding curves of the ten anti-CfaE antibodies are superimposed.

F=fecal collection, all animals; C=challenge; O=oral antibody administration; Q=SubQ antibody administration.

FIG. 8A is a set of images showing an SDS PAGE and a Western blot of dIgA2 (line 2) and sIgA2 (line 3) of 68-61 HuMab.

FIG. 8B is a set of images showing the activity of 68-61 dIgA2 and sIgA2 in mannose resistant hemagglutination assay of human group A erythrocyte. The minimal inhibitory concentration to prevent hemagglutination is 0.04 and 0.08 μg/ml for dIgA2 and sIgA2, respectively. The assay was repeated three times using different blood donors.

FIG. 8C is a graph showing a Caco-2 adhesion assay. The functionality of 68-61 dIgA2 and sIgA2 tested in a Caco-2 adhesion assay is shown.

DETAILED DESCRIPTION OF EMBODIMENTS OF THE INVENTION

I. Definitions

The terms "anti-CfaE antibody," "an antibody that binds to CfaE," and "an antibody that specifically binds to CfaE" refer to an antibody that is capable of binding CfaE with sufficient affinity such that the antibody is useful as a preventative, diagnostic, and/or therapeutic agent in targeting CfaE. In one embodiment, the extent of binding of an anti-CfaE antibody to an unrelated, non-CfaE protein is less than about 10% of the binding of the antibody to CfaE as measured, e.g., by a radioimmunoassay (RIA). In certain embodiments, an antibody that binds to CfaE has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$M or less, e.g. from $10^{-8}$ M to $10^{-13}$ M, e.g., from $10^{-9}$ M to $10^{-13}$ M).

The term "antibody" as used herein in the broadest sense encompasses various antibody structures, including but not limited to monoclonal antibodies, polyclonal antibodies, multispecific antibodies (e.g., bispecific antibodies), and antibody fragments so long as they exhibit the desired antigen-binding activity. An "antibody" can refer, for example, to a glycoprotein comprising at least two heavy chains (HCs) and two light chains (LCs) inter-connected by disulfide bonds, or an antigen binding portion thereof. Each heavy chain is comprised of a heavy chain variable region (VH) and a heavy chain constant region (CH). The heavy chain constant region may be comprised of three domains, CH1, CH2, and/or CH3. Each light chain is comprised of a light chain variable region (VL) and a light chain constant region (CL). The VH and VL regions can be further subdivided into regions of hypervariability, termed "complementarity determining regions" (CDRs), interspersed with regions that are more conserved, termed "framework regions" (FRs). Each VH and VL may be composed, for example, of three CDRs and four FRs, arranged from amino-terminus to carboxyl-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "colonization factor antigen I adhesin subunit E" or "CfaE" refers to subunit E of conolization factor antigen I (CFA/I). CFA/I is a filamentous structure on the surface of ETEC that is involved with ETEC adhesion to the small intestine, which allows the bacteria to cause infection.

The terms "full-length antibody," "intact antibody," and "whole antibody" are used herein interchangeably to refer to an antibody having a structure substantially similar to a native antibody structure or having heavy chains that contain an Fc region as defined herein.

The term "human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) Nature 368(6474): 856-859); Lonberg, N. (1994) Handbook of Experimental Pharmacology 113:49-101; Lonberg, N. and Huszar, D. (1995) Intern. Rev. Immunol. Vol. 13: 65-93, and Harding, F. and Lonberg, N. (1995) Ann. N.Y. Acad. Sci 764:536-546). However, the term "human antibody" does not include antibodies in which CDR sequences derived from the germline of another mammalian species, such as a mouse, have been grafted onto human framework sequences (i.e., humanized antibodies).

The term "monoclonal antibody," as used herein, refers to an antibody which displays a single binding specificity and affinity for a particular epitope. Accordingly, the term "human monoclonal antibody," or "HuMab," refers to an antibody which displays a single binding specificity and which has variable and constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

An "antibody fragment" refers to a molecule other than an intact antibody that comprises a portion of an intact antibody that specifically binds to the antigen (e.g., CFA/I or a CfaE protein thereof) to which the intact antibody binds. Examples of antibody fragments include, but are not limited to, Fv, Fab, Fab', Fab'-SH, F(ab')$_2$; diabodies; linear antibodies; single-chain antibody molecules (e.g., scFv); and multispecific antibodies formed from antibody fragments. These antibody fragments are obtained using conventional techniques, and the fragments are screened for utility in the same manner as are intact antibodies. Antibody fragments can be produced by recombinant DNA techniques, or by enzymatic or chemical cleavage of intact immunoglobulins.

The term "about" as used herein refers to the usual error range for the respective value readily known to the skilled person in this technical field. Reference to "about" a value or parameter herein includes (and describes) embodiments that are directed to that value or parameter per se.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described below.

The term "$K_D$," as used herein, is intended to refer to the dissociation equilibrium constant of a particular antibody-antigen interaction. Typically, the antibodies of the invention bind to CfaE with a dissociation equilibrium constant ($K_D$)

of less than about $10^{-6}$ M, such as less than approximately $10^{-7}$ M, $10^{-8}$ M, $10^{-9}$ M, or $10^{-10}$ M or even lower when determined by surface plasmon resonance (SPR) technology in a BIACORE 3000 instrument using recombinant CfaE as the analyte and the antibody as the ligand.

A "disorder" is any condition that would benefit from treatment including, but not limited to, chronic and acute disorders or diseases including those pathological conditions which predispose the mammal to the disorder in question.

As used herein, the term "disorder associated with an enterotoxigenic *Escherichia coli* infection" or "disorder associated with an ETEC infection" refers to any disease, the onset, progression, or the persistence of the symptoms of which requires the participation of ETEC. An exemplary disorder associated with an ETEC infection is, for example, diarrhea.

The term "EC50," as used herein, refers to the concentration of an antibody or an antigen-binding portion thereof, which induces a response, either in an in vivo or an in vitro assay, which is 50% of the maximal response (i.e., halfway between the maximal response and the baseline).

The terms "effective amount," "effective dose," and "effective dosage" as used herein are defined as an amount sufficient to achieve, or at least partially achieve, the desired effect. The term "therapeutically effective dose" or "therapeutically effective amount" is defined as an amount sufficient to prevent, cure, or at least partially arrest, the disease (e.g., diarrhea) and its complications in a patient already suffering from the disease or at risk of developing the disease. Amounts effective for this use will depend upon the severity of the disorder being treated and the general state of the patient's own immune system.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods of determining spatial conformation of epitopes include techniques in the art and those described herein, for example, x-ray crystallography and 2-dimensional nuclear magnetic resonance. See, for example, Epitope Mapping Protocols in Methods in Molecular Biology, Vol. 66, G. E. Morris, Ed. (1996). Epitopes can also be defined by point mutations in the target protein (e.g., CfaE), which affect the binding of the antibody (e.g., monoclonal antibody).

The term "host cell," as used herein, is intended to refer to a cell into which an expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "isolated antibody" is one which has been identified and separated and/or recovered from a component of its natural environment and/or is substantially free of other antibodies having different antigenic specificities (e.g., an isolated antibody that specifically binds to CfaE is substantially free of antibodies that specifically bind antigens other than CfaE). Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie™ blue or, preferably, silver stain. Isolated antibody includes the antibody in situ within recombinant cells since at least one component of the antibody's natural environment will not be present. Similarly, isolated antibody includes the antibody in medium around recombinant cells. Ordinarily, however, isolated antibody will be prepared by at least one purification step.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid," as used herein in reference to nucleic acids molecules encoding antibodies or antibody portions (e.g., VH, VL, CDRs) that bind to CfaE, is intended to refer to a nucleic acid molecule in which the nucleotide sequences encoding the antibody or antibody portion are free of other nucleotide sequences encoding antibodies that bind antigens other than CfaE, which other sequences may naturally flank the nucleic acid in human genomic DNA.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 3000 instrument, which can be performed, for example, using recombinant CfaE as the analyte and the antibody as the ligand. In some embodiments, binding by the antibody to the predetermined antigen is with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

A "subject" or an "individual" is a mammal. Mammals include, but are not limited to, domesticated animals (e.g., cows, sheep, cats, dogs, and horses), primates (e.g., humans and non-human primates such as monkeys), rabbits, deer, and rodents (e.g., mice and rats). In certain embodiments, the subject or individual is a human.

The terms "treat," "treating," and "treatment," as used herein, refer to preventative or therapeutic measures described herein. The methods of "treatment" employ administration to a subject in need of such treatment an antibody of the present invention, for example, a subject at risk of developing a disorder associated with ETEC infection or a subject having a disorder associated with ETEC infection, in order to prevent, cure, delay, reduce the severity of, or ameliorate one or more symptoms of the disorder or recurring disorder, or in order to prolong the survival of a subject beyond that expected in the absence of such treatment. In some embodiments, for example, the anti-CfaE antibodies of the invention would be administered to a subject at risk of developing a disorder associated with ETEC infection (e.g., a subject residing or traveling to a geographical location in which pathogenic ETEC is found). Accordingly, desirable effects of treatment include, but are not limited to, preventing occurrence of disease or disorder, such as a disorder associated with ETEC infection. Other desirable effects of treatment may include preventing recurrence of disease, alleviation of symptoms, diminishment of any direct or indirect pathological consequences of the disease, decreasing the rate of disease progression, amelioration or palliation of the disease state, and improved prognosis.

As used herein, "administering" is meant a method of giving a dosage of a compound (e.g., an anti-CfaE antibody of the invention or a nucleic acid encoding an anti-CfaE antibody of the invention) or a composition (e.g., a pharmaceutical composition, e.g., a pharmaceutical composition including an anti-CfaE antibody of the invention) to a subject. The compositions utilized in the methods described herein can be administered or formulated for administration, for example, intramuscularly, intravenously, intradermally, percutaneously, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularly, orally, topically, locally, by inhalation, by injection, by infusion, by continuous infusion, by localized perfusion bathing target cells directly, by catheter, by lavage, in cremes, or in lipid compositions. The method of administration can vary depending on various factors (e.g., the compound or composition being administered and the severity of the condition, disease, or disorder being treated). Preferably, the compound (e.g., anti-CfaE antibody 68-61, 68-48, or 68-90) or composition (e.g., pharmaceutical composition comprising anti-CfaE antibody 68-61, 68-48, or 68-90) is administered orally or formulated for oral administration.

As used herein, the term "vector" is meant to include, but is not limited to, a nucleic acid molecule (e.g., a nucleic acid molecule that is capable of transporting another nucleic acid to which it has been linked), a virus (e.g., a lentivirus or an adenovirus, e.g., a recombinant adeno-associated virus (rAAV)), cationic lipid (e.g., liposome), cationic polymer (e.g., polysome), virosome, nanoparticle, or dentrimer. Accordingly, one type of vector is a viral vector, wherein additional DNA segments (e.g., transgenes, e.g., transgenes encoding the heavy and/or light chain genes of an anti-CfaE antibody of the invention) may be ligated into the viral genome, and the viral vector may then be administered (e.g., by electroporation, e.g., electroporation into muscle tissue) to the subject in order to allow for transgene expression in a manner analogous to gene therapy. Another type of vector is a "plasmid," which refers to a circular double stranded DNA loop into which additional DNA segments may be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids.

II. Compositions and Methods

In one aspect, the invention is based, in part, on anti-colonization factor antigen I adhesin subunit E (CfaE) antibodies. Antibodies of the invention are useful, for example, for treating a subject having, or at risk of developing, a disorder associated with an enterotoxigenic *Escherichia coli* (ETEC) infection.

A. Anti-CfaE Antibodies

The invention provides isolated antibodies that bind to the CfaE of ETEC.

In one aspect, the invention provides isolated antibodies that specifically bind to CfaE. In some instances, the antibody may include the following complementarity determining regions (CDRs): (a) a CDR-H1 comprising the amino acid sequence of GGTFSSFAIS (SEQ ID NO: 1); (b) a CDR-H2 comprising the amino acid sequence of RIIPIL-DIVKYAQRFQG (SEQ ID NO: 2); (c) a CDR-H3 comprising the amino acid sequence of ARDDIAGSDFDI (SEQ ID NO: 3), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-3, and/or (ii) one, two, or three amino acid substitutions relative to the amino acid sequence of any one of SEQ ID NOs: 1-3. In some instances, the antibody includes the following CDRs: (a) a CDR-L1 comprising the amino acid sequence of QGISSW (SEQ ID NO: 4); (b) a CDR-L2 comprising the amino acid sequence of AAS (SEQ ID NO: 5); and (c) a CDR-L3 comprising the amino acid sequence of QQYTSYPYT (SEQ ID NO: 6), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 4-6, and/or (ii) one, two, or three amino acid substitutions relative to the amino acid sequence of any one of SEQ ID NOs: 4-6.

In some instances, the anti-CfaE antibodies may include the following heavy chain framework regions (FRs): (a) an FR-H1 comprising the amino acid sequence of QVQLVQS-GAEVKNPGSSVRVSCEAS (SEQ ID NO: 7); (b) an FR-H2 comprising the amino acid sequence of WVRQAPGQGLEWMG (SEQ ID NO: 8); (c) an FR-H3 comprising the amino acid sequence of RVTISADKST-STAYMELSSLRSEGTAVYYC (SEQ ID NO: 9); and (d) an FR-H4 comprising the amino acid sequence of WGQGTMVTVSSAST (SEQ ID NO: 10), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 7-10.

In some instances, the anti-CfaE antibodies may include the following light chain FRs: (a) an FR-L1 comprising the amino acid sequence of DIQMTQSPSSLSASVGDRVTIT-CRAS (SEQ ID NO: 11); (b) an FR-L2 comprising the amino acid sequence of LAWYQQKPEKAPKSLIY (SEQ ID NO: 12); (c) an FR-L3 comprising the amino acid sequence of SLQSGVPSRFSGSGSGTDFTLTISSLQPED-FATYYC (SEQ ID NO: 13); and (d) an FR-L4 comprising the amino acid sequence of FGQGTKLEIK (SEQ ID NO: 14), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 11-14.

For example, the antibody includes the following six CDRs: (a) a CDR-H1 comprising the amino acid sequence of GGTFSSFAIS (SEQ ID NO: 1); (b) a CDR-H2 comprising the amino acid sequence of RIIPILDIVKYAQRFQG (SEQ ID NO: 2); (c) a CDR-H3 comprising the amino acid sequence of ARDDIAGSDFDI (SEQ ID NO: 3); (d) a CDR-L1 comprising the amino acid sequence of QGISSW (SEQ ID NO: 4); (e) a CDR-L2 comprising the amino acid sequence of AAS (SEQ ID NO: 5); and (f) a CDR-L3 comprising the amino acid sequence of QQYTSYPYT (SEQ ID NO: 6), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6, and/or (ii) one, two, or three amino acid substitutions relative to the amino acid sequence of any one of SEQ ID NOs: 1-6. In some instances, the antibody includes the following four heavy chain FRs: (a) an FR-H1 comprising the amino acid sequence of QVQLVQS-GAEVKNPGSSVRVSCEAS (SEQ ID NO: 7); (b) an FR-H2 comprising the amino acid sequence of WVRQAPGQGLEWMG (SEQ ID NO: 8); (c) an FR-H3 comprising the amino acid sequence of RVTISADKST-STAYMELSSLRSEGTAVYYC (SEQ ID NO: 9); and (d) an FR-H4 comprising the amino acid sequence of WGQGTMVTVSSAST (SEQ ID NO: 10), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 7-10. In some instances, the antibody includes the following four light chain FRs: (a) an FR-L1 comprising the amino acid sequence of DIQMTQSPSSLSASVGDRVTITCRAS (SEQ ID NO: 11); (b) an FR-L2 comprising the amino acid sequence of LAWYQQKPEKAPKSLIY (SEQ ID NO: 12); (c) an FR-L3 comprising the amino acid sequence of SLQSGVPSRFSGSGSGTDFTLTISSLQPEDFATYYC (SEQ ID NO: 13); and (d) an FR-L4 comprising the amino acid sequence of FGQGTKLEIK (SEQ ID NO: 14), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 11-14. In some instances, the antibody comprises (a) a heavy chain variable domain (VH) sequence having at least 90% sequence identity (e.g., at least 91%, 92%, 93%, 94%, 95%, 96%, 97%, 98%, or 99% sequence identity) to, or the sequence of, SEQ ID NO: 15; (b) a light chain variable domain (VL) sequence having at least 90% sequence identity (e.g., at least 91%, 92%, 93%, 94%, 95%, 96%, 97%, 98%, or 99% sequence identity) to, or the sequence of, SEQ ID NO: 16; or (c) a VH sequence as in (a) and a VL sequence as in (b). In particular instances, the antibody is the exemplary anti-CfaE antibody 68-61.

In some instances, the antibody may include the following CDRs: (a) a CDR-H1 comprising the amino acid sequence of GGSFSGYSWS (SEQ ID NO: 17); (b) a CDR-H2 comprising the amino acid sequence of EIYHSG-STNYNPSLKS (SEQ ID NO: 18); (c) a CDR-H3 comprising the amino acid sequence of ARENLQGYYYYGMDV (SEQ ID NO: 19), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 17-19, and/or (ii) one, two, or three amino acid substitutions relative to the amino acid sequence of any one of SEQ ID NOs: 17-19. In some instances, the antibody includes the following CDRs: (a) a CDR-L1 comprising the amino acid sequence of QGISSS (SEQ ID NO: 20); (b) a CDR-L2 comprising the amino acid sequence of DAS (SEQ ID NO: 21); and (c) a CDR-L3 comprising the amino acid sequence of QQFNSYPRT (SEQ ID NO: 22), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 20-22, and/or (ii) one, two, or three amino acid substitutions relative to the amino acid sequence of any one of SEQ ID NOs: 20-22.

In some instances, the anti-CfaE antibodies may include the following heavy chain FRs: (a) an FR-H1 comprising the amino acid sequence of QVQLQQWGAGLLKPSETLSLT-CAVY (SEQ ID NO: 23); (b) an FR-H2 comprising the amino acid sequence of WIRQSPGKGLEWIG (SEQ ID NO: 24); (c) an FR-H3 comprising the amino acid sequence of RVTISGDTSKNQFSLKLSSVTAADTAVYYC (SEQ ID NO: 25); and (d) an FR-H4 comprising the amino acid sequence of WGQGTTVTVSSAST (SEQ ID NO: 26), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 23-26.

In some instances, the anti-CfaE antibodies may include the following light chain FRs: (a) an FR-L1 comprising the amino acid sequence of AIQLTQSPSSLSASVGDRVTIT-CRAS (SEQ ID NO: 27); (b) an FR-L2 comprising the amino acid sequence of LAWYQQKPGKAPKLLIY (SEQ ID NO: 28); (c) an FR-L3 comprising the amino acid sequence of SLESGVPSRFSGSGSGTDFTLTISSLQPED-FATYYC (SEQ ID NO: 29); and (d) an FR-L4 comprising the amino acid sequence of FGQGTKVEIK (SEQ ID NO: 30), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 27-30.

In another example, the antibody includes the following six CDRs: (a) a CDR-H1 comprising the amino acid sequence of GGSFSGYSWS (SEQ ID NO: 17); (b) a CDR-H2 comprising the amino acid sequence of EIYHSG-STNYNPSLKS (SEQ ID NO: 18); (c) a CDR-H3 comprising the amino acid sequence of ARENLQGYYYYGMDV (SEQ ID NO: 19); (d) a CDR-L1 comprising the amino acid sequence of QGISSS (SEQ ID NO: 20); (e) a CDR-L2 comprising the amino acid sequence of DAS (SEQ ID NO: 21); and (f) a CDR-L3 comprising the amino acid sequence of QQFNSYPRT (SEQ ID NO: 22), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 17-22, and/or (ii) one, two, or three amino acid substitutions relative to the amino acid sequence of any one of SEQ ID NOs: 17-22. In some instances, the antibody includes the following four heavy chain FRs: (a) an FR-H1 comprising the amino acid sequence of QVQLQQW-GAGLLKPSETLSLTCAVY (SEQ ID NO: 23); (b) an FR-H2 comprising the amino acid sequence of WIRQSPGKGLEWIG (SEQ ID NO: 24); (c) an FR-H3 comprising the amino acid sequence of RVTIS-GDTSKNQFSLKLSSVTAADTAVYYC (SEQ ID NO: 25); and (d) an FR-H4 comprising the amino acid sequence of WGQGTTVTVSSAST (SEQ ID NO: 26), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 23-26. In some instances, the antibody includes the following four light chain FRs: (a) an FR-L1 comprising the amino acid sequence of AIQLTQSPSSLSASVGDRVTITCRAS (SEQ ID NO: 27); (b) an FR-L2 comprising the amino acid sequence of LAWYQQKPGKAPKLLIY (SEQ ID NO: 28); (c) an FR-L3 comprising the amino acid sequence of SLESGVPSRFSGSGSGTDFTLTISSLQPEDFATYYC (SEQ ID NO: 29); and (d) an FR-L4 comprising the amino acid sequence of FGQGTKVEIK (SEQ ID NO: 30), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 27-30. In some instances, the antibody comprises (a) a VH sequence having at least 90% sequence identity (e.g., at least 91%, 92%, 93%, 94%, 95%, 96%, 97%, 98%, or 99% sequence identity) to, or the sequence of, SEQ ID NO: 31; (b) a VL sequence having at least 90% sequence identity (e.g., at least 91%, 92%, 93%, 94%, 95%, 96%, 97%, 98%, or 99% sequence identity) to, or the sequence of, SEQ ID NO: 32; or (c) a VH sequence as in (a) and a VL sequence as in (b). In particular instances, the antibody is the exemplary anti-CfaE antibody 68-48.

In some instances, the antibody may include the following CDRs: (a) a CDR-H1 comprising the amino acid sequence of GGSFSAYYWS (SEQ ID NO: 33); (b) a CDR-H2 comprising the amino acid sequence of EINHSGNTNYNPSLES (SEQ ID NO: 34); (c) a CDR-H3 comprising the amino acid sequence of ARNWGPNAFDI (SEQ ID NO: 35), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 33-35, and/or (ii) one, two, or three amino acid substitutions relative to the amino acid sequence of any one of SEQ ID NOs: 33-35. In some instances, the antibody includes the following CDRs: (a) a CDR-L1 comprising the amino acid sequence of QDITSW (SEQ ID NO: 36); (b) a CDR-L2 comprising the amino acid sequence of AAS (SEQ ID NO: 37); and (c) a CDR-L3 comprising the amino acid sequence of QQANIFPYT (SEQ ID NO: 38), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 36-38, and/or (ii) one, two, or three amino acid substitutions relative to the amino acid sequence of any one of SEQ ID NOs: 36-38.

In some instances, the anti-CfaE antibodies may include the following heavy chain FRs: (a) an FR-H1 comprising the amino acid sequence of QVQLQQWGAGLLKPSETLSLT-CAVY (SEQ ID NO: 39); (b) an FR-H2 comprising the amino acid sequence of WIRQPPGKGLEWIG (SEQ ID NO: 40); (c) an FR-H3 comprising the amino acid sequence of RVTISVDTSKNQVSLKQSSVTAADTAVYYC (SEQ ID NO: 41); and (d) an FR-H4 comprising the amino acid sequence of WGRGTMVTVSSAST (SEQ ID NO: 42), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 39-42.

In some instances, the anti-CfaE antibodies may include the following light chain FRs: (a) an FR-L1 comprising the amino acid sequence of DIQMTQSPSSVSASVGDRVTIT-CRAS (SEQ ID NO: 43); (b) an FR-L2 comprising the amino acid sequence of LVWYQHKPGKAPKLLIY (SEQ ID NO: 44); (c) an FR-L3 comprising the amino acid sequence of SLQSGVPSRFSGSGSGTDFTLTISSLQPED-FATYYC (SEQ ID NO: 45); and (d) an FR-L4 comprising the amino acid sequence of FGQGTKLEIK (SEQ ID NO: 46), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 43-46.

In another example, the antibody includes the following six CDRs: (a) a CDR-H1 comprising the amino acid sequence of GGSFSAYYWS (SEQ ID NO: 33); (b) a CDR-H2 comprising the amino acid sequence of EINHSGNTNYNPSLES (SEQ ID NO: 34); (c) a CDR-H3 comprising the amino acid sequence of ARNWGPNAFDI (SEQ ID NO: 35); (d) a CDR-L1 comprising the amino acid sequence of QDITSW (SEQ ID NO: 36); (e) a CDR-L2 comprising the amino acid sequence of AAS (SEQ ID NO: 37); and (f) a CDR-L3 comprising the amino acid sequence of QQANIFPYT (SEQ ID NO: 38), or a combination of one or more of the above CDRs and one or more variants thereof having (i) at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 33-38, and/or (ii) one, two, or three amino acid substitutions relative to the amino acid sequence of any one of SEQ ID NOs: 33-38. In some instances, the antibody includes the following four heavy chain FRs: (a) an FR-H1 comprising the amino acid sequence of QVQLQQW-GAGLLKPSETLSLTCAVY (SEQ ID NO: 39); (b) an FR-H2 comprising the amino acid sequence of WIRQPPGKGLEWIG (SEQ ID NO: 40); (c) an FR-H3 comprising the amino acid sequence of RVTISVDTSKNQVSLKQSSVTAADTAVYYC (SEQ ID NO: 41); and (d) an FR-H4 comprising the amino acid sequence of WGRGTMVTVSSAST (SEQ ID NO: 42), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 39-42. In some instances, the antibody includes the following four light chain FRs: (a) an FR-L1 comprising the amino acid sequence of DIQMTQSPSSVSASVGDRVTITCRAS (SEQ ID NO: 43); (b) an FR-L2 comprising the amino acid sequence of LVWYQHKPGKAPKLLIY (SEQ ID NO: 44); (c) an FR-L3 comprising the amino acid sequence of SLQSGVPSRFSGSGSGTDFTLTISSLQPEDFATYYC (SEQ ID NO: 45); and (d) an FR-L4 comprising the amino acid sequence of FGQGTKLEIK (SEQ ID NO: 46), or a combination of one or more of the above FRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 43-46. In some instances, the antibody comprises (a) a VH sequence having at least 90% sequence identity (e.g., at least 91%, 92%, 93%, 94%, 95%, 96%, 97%, 98%, or 99% sequence identity) to, or the sequence of, SEQ ID NO: 47; (b) a VL sequence having at least 90% sequence identity (e.g., at least 91%, 92%, 93%, 94%, 95%, 96%, 97%, 98%, or 99% sequence identity) to, or the sequence of, SEQ ID NO: 48; or (c) a VH sequence as in (a) and a VL sequence as in (b). In particular instances, the antibody is the exemplary anti-CfaE antibody 68-90.

Antibodies of the invention may, for example, be monoclonal, human, humanized, or chimeric. The antibodies can be full-length antibodies or antibody fragments thereof (e.g., an antibody fragment that binds CfaE). The antibody fragment may be selected from the group consisting of Fab, Fab'-SH, Fv, scFv, and (Fab')$_2$ fragments. In some instances, the antibody is an IgG antibody (e.g., an IgG1 antibody). An antibody of the invention may have a half-life of 3 days (e.g., 1 week, e.g., ≥2 weeks, e.g., ≥1 month, e.g., ≥2 months, e.g., ≥3 months, e.g., ≥4 months, e.g., ≥5 months, e.g., ≥6 months).

In a further aspect, an anti-CfaE antibody according to any of the above embodiments may incorporate any of the features, singly or in combination, as described in Sections 1-5 below.

1. Antibody Affinity

In certain embodiments, an antibody provided herein may have a dissociation constant ($K_D$) of ≤10 µM, ≤1 µM, ≤100 nM, ≤10 nM, ≤1 nM, ≤0.1 nM, or ≤0.01 nM.

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20©) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N' (3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{on}/k_{off}$. See, for example, Chen et al., J. Mol. Biol. 293:865-881 (1999). If the on-rate exceeds $10^6 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, which are known in the art. Also included are diabodies, which have two antigen-binding sites that may be bivalent or bispecific, as is known in the art. Triabodies and tetrabodies are also known. Single-domain antibodies are also antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody (e.g., a human monoclonal antibody (HuMab), e.g., an anti-CfaE HuMab). Human antibodies can be produced using various techniques known in the art.

In some instances, human antibodies are obtained by cloning the heavy and light chain genes directly from human B cells obtained from a human subject. The B cells are separated from peripheral blood (e.g., by flow cytometry, e.g., FACS), stained for B cell marker(s), and assessed for antigen binding. The RNA encoding the heavy and light chain variable regions (or the entire heavy and light chains) is extracted and reverse transcribed into DNA, from which the antibody genes are amplified (e.g., by PCR) and sequenced. The known antibody sequences can then be used to express recombinant human antibodies against a known target antigen (e.g., CfaE).

In some instances, human antibodies may be prepared by administering an immunogen (e.g., CfaE) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. Human variable regions from intact antibodies generated by such animals may be further modified, for example, by combining with a different human constant region.

In some instances, human antibodies can also be made by hybridoma-based methods, as described in further detail below. Human myeloma and mouse-human heteromyeloma cell lines for the production of human monoclonal antibodies have been described.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Antibody Variants

In certain embodiments, amino acid sequence variants of the anti-CfaE antibodies of the invention are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

In certain embodiments, antibody variants having one or more amino acid substitutions are provided. Sites of interest for substitutional mutagenesis include the CDRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |

TABLE 1-continued

Exemplary and Preferred Amino Acid Substitutions

| Original Residue | Exemplary Substitutions | Preferred Substitutions |
|---|---|---|
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (\N) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Iie;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g., binding affinity).

Alterations (e.g., substitutions) may be made in CDRs, for example, to improve antibody affinity. Such alterations may be made in CDR "hotspots," i.e., residues encoded by codons that undergo mutation at high frequency during the somatic maturation process, and/or residues that contact antigen, with the resulting variant VH or VL being tested for binding affinity. Affinity maturation by constructing and reselecting from secondary libraries is known in the art. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant VH and VL sequences provided above, each CDR either is unaltered, or contains no more than one, two, or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, And Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

In certain embodiments, alternations may be made to the Fc region of an antibody. These alterations can be made alone, or in addition to, alterations to one or more of the antibody variable domains (i.e., VH or VL regions) or regions thereof (e.g., one or more CDRs or FRs). The alterations to the Fc region may result in enhanced antibody effector functions (e.g., complement-dependent cytotoxicity (CDC)), for example, by increasing C1q avidity to opsonized cells. Exemplary mutations that enhance CDC include, for example, Fc mutations E345R, E430G, and S440Y. Accordingly, anti-CfaE antibodies of the invention may contain one or more CDC-enhancing Fc mutations, which promote IgG hexamer formation and the subsequent recruitment and activation of C1, the first component of complement (see, e.g., Diebolder et al. *Science.* 343: 1260-1263, 2014).

In certain embodiments, alterations of the amino acid sequences of the Fc region of the antibody may alter the half-life of the antibody in the host. Certain mutations that alter binding to the neonatal Fc receptor (FcRn) may extend half-life of antibodies in serum. For example, antibodies that have tyrosine in heavy chain position 252, threonine in position 254, and glutamic acid in position 256 of the heavy chain can have dramatically extended half-life in serum (see, e.g., U.S. Pat. No. 7,083,784).

B. Production of Human Antibodies to CfaE
1. Immunizations

The present invention features human monoclonal antibodies (HuMabs) that bind CfaE. Exemplary human monoclonal antibodies that bind CfaE include 68-61, 68-48, and 68-90.

Human monoclonal antibodies of the invention can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for generating hybridomas which produce human monoclonal antibodies of the invention is the murine system. Hybridoma production in the mouse is well known in the art, including immunization protocols and techniques for isolating and fusing immunized splenocytes.

In one embodiment, human monoclonal antibodies directed against CfaE are generated using transgenic mice carrying parts of the human immune system rather than the mouse system. In one embodiment, the invention employs transgenic mice, referred to herein as "HuMAb mice," which contain a human immunoglobulin gene miniloci that encodes unrearranged human heavy ($\mu$ and $\gamma$) and $\kappa$ light chain immunoglobulin sequences, together with targeted mutations that inactivate the endogenous $\mu$ and $\kappa$ chain loci. Accordingly, the mice exhibit reduced expression of mouse IgM or $\kappa$, and in response to immunization, the introduced human heavy and light chain transgenes undergo class switching and somatic mutation to generate high affinity human IgG $\kappa$ monoclonal antibodies.

To generate fully human monoclonal antibodies to CfaE, transgenic mice containing human immunoglobulin genes and inactivated mouse heavy and kappa light chain genes (Bristol-Myers Squib) can be immunized with a purified or enriched preparation of the CfaE antigen (e.g., the N-terminal adhesion domain of CfaE) and/or cells expressing CfaE, as described, for example, by Lonberg et al. (1994) Nature 368(6474): 856-859; Fishwild et al. (1996) Nature Biotechnology 14: 845-851 and WO 98/24884. As described herein, HuMAb mice are immunized either with recombinant CfaE proteins or cell lines expressing CfaE as immunogens. Alternatively, mice can be immunized with DNA encoding CfaE. Preferably, the mice will be 6-16 weeks of age (e.g., 6-10 weeks of age) upon the first infusion. For example, a purified or enriched preparation ($10^{-100}$ μg, e.g., 50 μg) of the recombinant CfaE antigen can be used to immunize the HuMAb mice, for example, intraperitoneally. In the event that immunizations using a purified or enriched preparation of the CfaE antigen do not result in antibodies, mice can also be immunized with cells expressing CfaE proteins, e.g., a cell line, to promote immune responses.

Cumulative experience with various antigens has shown that the HuMAb transgenic mice respond best when initially immunized intraperitoneally (IP) or subcutaneously (SC) with antigen in complete Freund's adjuvant, followed by every other week IP/SC immunizations (up to a total of 10) with antigen in incomplete Freund's adjuvant. The immune response can be monitored over the course of the immunization protocol with plasma samples being obtained by retro-orbital or facial vein bleeds. The plasma can be screened by ELISA (as described below), and mice with sufficient titers of anti-CfaE human immunoglobulin can be used for fusions. Mice can be boosted intravenously with antigen 3 days before sacrifice and removal of the spleen.

2. Generation of Hybridomas Producing HuMabs to CfaE

To generate hybridomas producing human monoclonal antibodies to CfaE, splenocytes and lymph node cells from immunized mice can be isolated and fused to an appropriate immortalized cell line, such as a mouse myeloma cell line (e.g., P3X-AG8.653). The resulting hybridomas can then be screened for the production of antigen-specific antibodies. For example, single cell suspensions of splenic lymphocytes from immunized mice can be fused to SP2/0-AG8.653 non-secreting mouse myeloma cells (ATCC, CRL 1580) with 50% PEG (w/v). Cells can be plated at approximately $1 \times 10^5$ in flat bottom microtiter plate, followed by a two week incubation in selective medium containing besides usual reagents 10% fetal Clone Serum, and 1×HAT (Sigma). After approximately two weeks, cells can be cultured in medium in which the HAT is replaced with HT. Individual wells can then be screened by ELISA for human anti-CfaE monoclonal IgM and IgG antibodies, or for binding to the surface of ETEC expressing CfaE proteins by, for example, FLISA (fluorescence-linked immunosorbent assay). Once extensive hybridoma growth occurs, medium can be observed usually after $10^{-14}$ days. The antibody secreting hybridomas can be re-plated, screened again, and, if still positive for human IgG, anti-CfaE monoclonal antibodies can be subcloned at least twice by limiting dilution. The stable subclones can then be cultured in vitro to generate antibody in tissue culture medium for characterization.

3. Generation of Transfectomas Producing HuMabs to CfaE

Human antibodies of the invention also can be produced in a host cell transfectoma using, for example, a combination of recombinant DNA techniques and gene transfection methods as is well known in the art. For example, in one embodiment, the gene(s) of interest, e.g., human antibody genes, can be ligated into an expression vector such as a eukaryotic expression plasmid. The purified plasmid with the cloned antibody genes can be introduced in eukaryotic host cells such as CHO-cells or NSO-cells or alternatively other eukaryotic cells like a plant derived cells, fungi or yeast cells. The method used to introduce these genes can be methods described in the art such as electroporation, lipofectine, lipofectamine or other. After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells. Alternatively these cloned antibody genes can be expressed in other expression systems such as E. coli or in complete organisms or can be synthetically expressed.

4. Recombinant Generation of HuMabs to CfaE

Anti-CfaE antibodies of the invention (e.g., anti-CfaE antibodies 68-61, 68-48, and 68-90, or variants thereof) may be produced using recombinant methods and compositions, for example, as described in U.S. Pat. No. 4,816,567. In one embodiment, isolated nucleic acid encoding an anti-CfaE antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-CfaE antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CfaE antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts.

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells, and myeloma cell lines such as Y0, NS0, and Sp2/0.

C. Characterization of Human Monoclonal Antibodies to CfaE

Sequence information for human monoclonal antibodies of the invention can be ascertained using sequencing techniques which are well known in the art.

Similarly, affinity of the antibodies for CfaE can also be assessed using standard techniques. For example, Biacore 3000 can be used to determine the affinity of HuMabs to CfaE. HuMabs are captured on the surface of a Biacore chip (GE healthcare), for example, via amine coupling (Sensor Chip CM5). The captured HuMabs can be exposed to various concentrations of CfaE in solution, and the $K_{on}$ and $K_{off}$ for an affinity ($K_D$) can be calculated, for example, by BIAevaluation software.

Human monoclonal antibodies of the invention can also be characterized for binding to CfaE using a variety of known techniques, such as ELISA, Western blot, etc. Generally, the antibodies are initially characterized by ELISA. Briefly, microtiter plates can be coated with purified CfaE in PBS, and then blocked with irrelevant proteins such as bovine serum albumin (BSA) diluted in PBS. Dilutions of plasma from CfaE-immunized mice are added to each well and incubated for 1-2 hours at 37° C. The plates are washed with PBS/Tween 20 and then incubated with a goat-anti-human IgG Fc-specific polyclonal reagent conjugated to alkaline phosphatase for 1 hour at 37° C. After washing, the plates are developed with ABTS substrate, and analyzed at OD of 405. Preferably, mice which develop the highest titers will be used for fusions.

In some instances, an ELISA assay as described above can be used to screen for antibodies and, thus, hybridomas that produce antibodies that show positive reactivity with the CfaE immunogen. Hybridomas that bind, preferably with high affinity, to CfaE can then be subcloned and further characterized. One clone from each hybridoma, which retains the reactivity of the parent cell (by ELISA), can then be chosen for making a cell bank, and for antibody purification.

In some instances, the antibodies are evaluated by a mannose-resistant hemagglutination (MRHA) assay of human group A erythrocytes. The MRHA assay is considered a surrogate method for assessment of ETEC adhesion to the intestinal mucosa (Hagberg et al., *Infect. Immun.* 31:564-570, 1981). In summary, the MRHA assay is performed as follows. First, ETEC cultures are taken from frozen cell banks and diluted in saline solution, reaching an $OD_{600\ nm}$ of 1 for the assay. Human erythrocytes type A+ are washed in saline solution and resuspended in the same solution. Serial antibody dilutions are prepared in a 96-well plate. The diluted ETEC and a solution of D-mannose are added to each well, then incubated at room temperature for 10 minutes. After incubation, the blood solution is added to the plates and mixed well, then allowed to sit stagnant at 4° C. for two hours. Hemagglutination is then observed without the aid of magnification. The absence of a pellet of red blood cells at the bottom of the well is indicative of positive hemagglutination.

In other instances, the antibodies are evaluated for their ability to inhibit binding of ETEC to intestinal cells by a Caco-2 cell adhesion assay. Briefly, Caco-2 cells are seeded and grown in 24-well tissue plates containing Dulbecco's modified Eagle's medium (DMEM), and frozen bacterial banks are streaked on CFA agar plates and grown overnight at 37° C. Bacteria are then resuspended in PBS and diluted until reaching an $OD_{600\ nm}$ of 0.1. Serial antibody dilutions are also prepared in a deep well plate. The antibody dilutions and bacteria are combined and allowed to shake at 300 rpm for one hour at room temperature. The antibody/bacteria mixture is then added to Caco-2 cells and incubated statically for 3 hours at 37° C. After incubation, cells are washed with PBS to remove non-adherent ETEC cells, then dislodged with trypsin, collected via centrifugation, and resuspended in PBS. Dilutions are plated on CFA agar plates and colonies are counted the next day. $IC_{50}$ is defined as a concentration of HuMAb needed to inhibit 50% of ETEC adhesion to Caco-2 cells compared to an irrelevant antibody.

In other instances, competition assays may be used to identify an antibody that competes with an anti-CfaE antibody of the invention for binding to CfaE. In certain embodiments, such a competing antibody binds to the same epitope (e.g., a linear or a conformational epitope) that is bound by an anti-CfaE antibody of the invention. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized CfaE is incubated in a solution comprising a first labeled antibody that binds to CfaE and a second unlabeled antibody that is being tested for its ability to compete with the first antibody for binding to CfaE. The second antibody may be present in a hybridoma supernatant. As a control, immobilized CfaE is incubated in a solution comprising the first labeled antibody but not the second unlabeled antibody. After incubation under conditions permissive for binding of the first antibody to CfaE, excess unbound antibody is removed, and the amount of label associated with immobilized CfaE is measured. If the amount of label associated with immobilized CfaE is substantially reduced in the test sample relative to the control sample, then that indicates that the second antibody is competing with the first antibody for binding to CfaE.

D. Pharmaceutical Compositions

In another aspect, the present invention provides a composition, e.g., a pharmaceutical composition, containing one or more (e.g., 1, 2, 3, or 4 or more) of the anti-CfaE human monoclonal antibodies (HuMabs), or antibody fragments thereof, of the present invention. The pharmaceutical compositions may be formulated together with a pharmaceutically acceptable carrier, excipient, or diluent. In some instances, the pharmaceutical compositions include two or more of the anti-CfaE HuMabs of the invention. Preferably, each of the antibodies of the composition binds to a distinct, pre-selected epitope of CfaE.

A pharmaceutical composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

The anti-CfaE antibodies of the invention may be orally administered as a pharmaceutical composition, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the anti-CfaE antibodies of the invention may be incorporated with an excipient and used in the form of ingestible tablets, buccal tablets, troches, capsules, elixirs, suspensions, syrups, and wafers. Oral formulations including antibodies are described in Jaison et al., *Nutrition Journal.* 14:22 (2015), which is incorporated herein by reference in its entirety. For example, the anti-CfaE antibodies may be formulated in a lyophilized composition, mixed into a liquid or a powder formulation. The anti-CfaE antibodies may also be formulated in enteric-coated capsules containing the antibodies. The composition formulated for oral administration may contain at least 0.01% (w/v) of the antibody. For example, the composition may contain about 0.1% to 70% (w/v) of the antibody, e.g., about 0.1% to 65% (w/v), about 0.1% to 65% (w/v), about 0.1% to 55% (w/v), about 0.1% to 50% (w/v), about 0.1% to 45% (w/v), about 0.1% to 40% (w/v), about 0.1% to 35% (w/v), about 0.1% to 30% (w/v), about 0.1% to 25% (w/v), about 0.1% to 20% (w/v), about 0.1% to 15% (w/v), about 0.1% to 10% (w/v), about 0.1% to 5% (w/v), about 0.1% to 2% (w/v), about 2% to 70% (w/v), or about 2% to 60% (w/v) of the antibody.

Pharmaceutical compositions of the invention also can be administered in combination therapy, i.e., combined with other agents. For example, the combination therapy can include a composition of the present invention with at least one or more additional therapeutic agents as necessary for the particular indication (e.g., diarrhea) being treated.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions.

Sustained-release preparations may be prepared. Suitable examples of sustained-release preparations include semipermeable matrices of solid hydrophobic polymers containing the antibody, which matrices are in the form of shaped articles, for example, films, or microcapsules.

The formulations to be used for in vivo administration are generally sterile. Sterility may be readily accomplished, e.g., by filtration through sterile filtration membranes. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, such as TWEEN® 80. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Alternatively, genes encoding the anti-CfaE antibodies of the invention may be delivered directly into the subject for expression rather than administering purified antibodies for prevention or therapy. For example, viral vectors, such as recombinant viruses, can be used to deliver the heavy and light chain genes. In one example, rAAV virus particles can be used to deliver anti-HIV monoclonal antibodies (Balazs et al. *Nature.* 481: 81, 2012). Antibody genes could also be effectively delivered by electroporation of muscle cells with plasmid DNA containing heavy and/or light chain genes (e.g., VH and/or VL genes) (Muthumani et al. *Hum Vaccin Immunother.* 10: 2253, 2013). Lentivirus vectors or other nucleic acids (e.g., RNA) capable of delivering transgenes could also be used to deliver antibody genes to establish serum antibody levels capable of prevention.

Also within the scope of the present invention are kits including human anti-CfaE antibodies of the invention and, optionally, instructions for use. The kits can further contain one or more additional reagents, such as a second, different anti-CfaE antibody having a complementary activity that binds to an epitope on CfaE that is distinct from the epitope to which the first anti-CfaE antibody binds.

E. Therapeutic Methods of the Invention

Any of the anti-CfaE antibodies of the invention (e.g., HuMabs anti-CfaE antibodies 68-61, 68-48, and 68-90) and compositions containing the antibodies can be used in a variety of in vitro and in vivo therapeutic applications.

In one aspect, the invention features a method of treating a subject having a disorder associated with an ETEC infection (e.g., diarrhea) comprising administering a therapeutically effective amount of a monoclonal antibody (e.g., a human monoclonal antibody) that specifically binds to CfaE, or a pharmaceutical composition thereof, thereby treating the subject.

In another aspect, an anti-CfaE antibody of the invention may be used in a method of treating a subject having a disorder associated with an ETEC infection. In one embodiment, the method comprises administering to a subject having such a disorder associated with an ETEC infection (e.g., diarrhea) a therapeutically effective amount of one or more (e.g., 1, 2, 3, or 4 or more) anti-CfaE antibodies of the invention or a pharmaceutical composition including the one or more anti-CfaE antibodies.

In another aspect, an anti-CfaE antibody of the invention may be used in a method of treating a subject at risk of developing a disorder associated with an ETEC infection (e.g., treating a subject at risk of developing a disorder associated with an ETEC infection with an anti-CfaE antibody of the invention in order to prevent the subject from developing a disorder associated with an ETEC infection, such as diarrhea). In one embodiment, the method comprises administering to a subject at risk of developing a disorder associated with an ETEC infection a therapeutically effective amount of one or more (e.g., 1, 2, 3, or 4 or more) anti-CfaE antibodies of the invention or a pharmaceutical composition including the one or more anti-CfaE antibodies. In some instances, a subject can be considered at risk of an ETEC infection if the subject is in a geographic region in which ETEC is commonly found (e.g., in Asia, the Middle East, Africa, and Central and South America). In other instances, subject can be considered at risk of an ETEC infection if the subject had travelled, or will travel, to a geographic region in which ETEC is commonly found.

Antibodies of the invention can be used either alone or in combination with other agents in a therapy. For instance, an antibody of the invention may be co-administered with at least one additional therapeutic agent. Such combination therapies encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-CfaE antibody (e.g., HuMabs anti-CfaE antibodies 68-61, 68-48, and 68-90) and administration of an additional therapeutic agent occur within about one month, or within about one, two or three weeks, or within about one, two, three, four, five, or six days, of each other.

An antibody of the invention, such as HuMabs anti-CfaE antibodies 68-61, 68-48, and 68-90, (and/or any additional therapeutic agent) can be administered by any suitable means, including oral, parenteral, intrapulmonary, and intranasal, and, if desired for local treatment, intralesional administration. Parenteral infusions include intramuscular, intravenous, intraarterial, intraperitoneal, or subcutaneous administration. Preferably, the antibodies are administered orally or subcutaneously. In certain instances, antibody genes (e.g., genes encoding any one or more of the anti-CfaE antibodies of the invention could be administered as a gene therapy to produce the one or more anti-CfaE antibodies in the subject using either DNA vectors or viral vectors (e.g., rAAV vectors). Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, such as diarrhea, the appropriate dosage of an antibody of the invention (when used alone or in combination with one or more other additional therapeutic agents) will depend on the type of disease to be prevented/treated, the duration of effective antibody concentration required, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. In some embodiments, a dosing schedule can include delivery, for example oral delivery, 1-3 days before a subject is at risk of developing a disorder associated with an ETEC infection (e.g., −3 days, −2 days, and/or −1 day), on the day a subject is at risk of developing a disorder associated with an ETEC infection (e.g., 0 day), and/or 1-3 days after a subject was at risk of developing a disorder associated with an ETEC infection (e.g., +1 day, +2 days, and/or +3 days). In some embodiments, a dosing schedule can include delivery, for example oral delivery, on the day before a subject is at risk of developing a disorder associated with an ETEC infection (e.g., −1 days), the day a subject is at risk of developing a disorder associated with an ETEC infection (e.g., 0 day), and/or on the day after a subject is at risk of developing a disorder associated with an ETEC infection (e.g., +1 day).

As a general proposition, the therapeutically effective amount of the anti-CfaE antibody administered to human will be in the range of about 0.01 to about 100 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.1 to about 10 mg/kg, or about 1 to about 10 mg/kg administered one (single administration) or more times (multiple administrations, e.g., daily administrations). In one example, the antibody used is about 10 mg/kg, preferably administered orally. In one embodiment, an anti-CfaE antibody described herein is administered to a human at a flat dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.01 mg/kg to about 10 mg/kg. Such doses may be administered intermittently, for example, every week or every three weeks (e.g., such that the patient receives from about two to about twenty, or, for example, about six doses of the anti-CfaE antibody). An initial higher loading dose, followed by one or more lower doses may be administered. The progress of this therapy is easily monitored by conventional techniques and assays.

Actual dosage levels of the active ingredients in the pharmaceutical compositions of the present invention may be varied so as to obtain an amount of the active ingredient which is effective to achieve the desired therapeutic response and duration for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved. In general, a suitable daily dose of compositions of the invention will be that amount of the compound which is the lowest dose effective to produce a therapeutic effect. Such an effective dose will generally depend upon the factors described above. If desired, the effective daily dose of therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. The liposomes may comprise one or more moieties which are selectively transported into specific cells or organs, thus enhance targeted drug delivery. Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134), different species of which may comprise the formulations of the inventions, as well as components of the invented molecules; p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273. In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

In some instances, the antibody-based therapy may be combined with an additional therapy for more efficacious treatment (e.g., additive or synergistic treatment) of the subject. Accordingly, subjects treated with antibodies of the invention can be additionally administered (prior to, simultaneously with, or following administration of a human antibody of the invention) with another therapeutic agent which enhances or augments the therapeutic effect of the human antibodies.

F. Methods and Compositions for Diagnostics and Detection

In certain embodiments, any of the anti-CfaE antibodies of the invention are useful for in vitro or in vivo detection of the presence of CfaE in a biological sample. The term "detecting" as used herein encompasses quantitative or qualitative detection. In certain embodiments, a biological sample comprises a cell or tissue.

In one embodiment, an anti-CfaE antibody for use in a method of diagnosis (e.g., diagnosis of a disorder associated with an ETEC infection) or detection (e.g., detection of an ETEC infection) is provided. In a further aspect, a method of detecting the presence of CfaE in a biological sample is provided. In certain embodiments, the method comprises contacting the biological sample with an anti-CfaE antibody as described herein under conditions permissive for binding of the anti-CfaE antibody to CfaE, and detecting whether a complex is formed between the anti-CfaE antibody and CfaE. Such method may be an in vitro or in vivo method.

In certain embodiments, labeled anti-CfaE antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

G. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. In some embodiments, the invention provides a kit comprising an antibody of the invention and a package insert with instructions for using the antibody for treating a subject having or at risk of developing a disorder associated with an ETEC infection. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Other embodiments of the present invention are described in the following Examples. The present invention is further illustrated by the following examples which should not be construed as further limiting. The contents of Sequence Listing, figures and all references, patents and published patent applications cited throughout this application are expressly incorporated herein by reference.

III. Examples

The following are examples of the methods and compositions of the invention. It is understood that various other embodiments may be practiced, given the description provided herein.

Example 1. Materials and Methods

ETEC Test Strains

Enterotoxigenic *E. coli* strain H10407 expressing CFA/I fimbriae was purchased from ATCC (ATCC® 35401™). ETEC strain H10407 was cultured on 2% agar containing 1% Casamino Acids (Sigma) and 0.15% yeast extract (Fisher Bioreagents) plus 0.005% $MgSO_4$ (Sigma) and 0.0005% $MnCl_2$ (Sigma) (CFA agar plates) overnight at 37° C. $1\times10^8$ colony forming units/mL were resuspended in 20% glycerol (Sigma) in PBS solution, and kept frozen at −80° C. until needed.

Antigen Cloning, Expression, Purification

The nucleic acid sequences of N-terminal adhesin domain of CfaE (GenBank M55661) was cloned into a pMAL-C5X vector (Addgene) in-frame with a maltose-binding protein (MBP) tag to express as periplasmic proteins with improved solubility (MBP-CfaE-N).

The donor strand complement was included to ensure the overall protein expression and stability as reported (Poole et al., *Mol. Microbiol.* 63:1372-84, 2007). All cloned constructs were transformed into SHuffle® T7 Competent *Escherichia coli* (NEB), and expression was induced with 1 mM IPTG. Bacteria were lysed, and proteins were purified with amylose resin (NEB) and eluted with 20 and 50 mM Maltose (Sigma).

Mouse Immunization, Hybridoma Generation, and Antibody Cloning

Transgenic mice containing human immunoglobulin genes and inactivated mouse heavy and κ light chain genes (Bristol-Myers Squib) were immunized with 50 μg of MBP-CfaE-N weekly with the Sigma adjuvant system (Sigma) for 6-10 weeks. Anti-CfaE titer in mouse serum was measured by enzyme-linked immunosorbent assay (ELISA). Hybridomas were generated following a standard PEG fusion protocol (Wang et al., *J. Infect. Dis.* 214:205-11, 2016). Hybridoma supernatants were screened for reactivity to MBP-CfaE-N, and positive cell clones were selected for antibody sequencing. The heavy chain and light chain variable regions were amplified from hybridoma cells and cloned into two pcDNA 3.1 (Thermo Fisher) vectors containing K light constant and IgG1 heavy constant chain respectively as previously described (Wang et al., J. Infect. Dis. 214:205-11, 2016).

IgA Class Switching

Figure 6B:
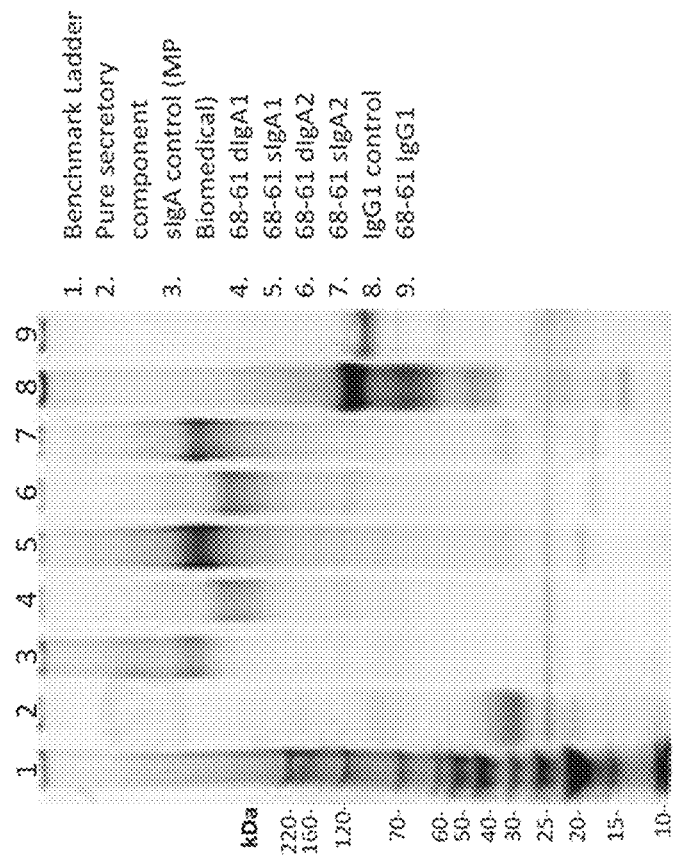
FIG. 6B is a gel showing SDS-PAGE of sIgA, dIgA, and IgG of 68-61 HuMAb. All samples were run on a NuPage 3-8% Tris-Acetate gel and stained with SPYRO Ruby.
Figure 6A:
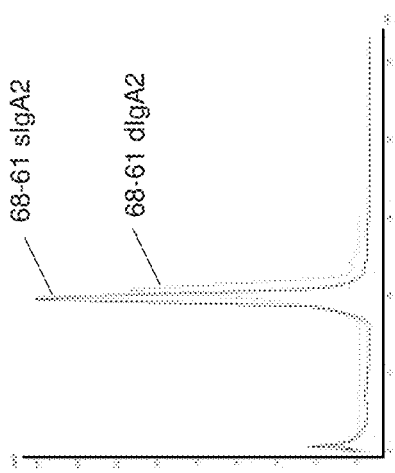
FIG. 6A is a graph showing size exclusion chromatography profiles of purified 68-61 secretory IgA2 (sIgA2) and 68-61 dimeric IgA2 (dIgA2). The single peak of each sample demonstrates >97% purity.

Primers were designed to amplify the variable heavy chain of each IgG antibody, and products were digested and ligated into a pcDNA 3.1 vector containing heavy constant IgA1 and IgA2 chains. Each vector was transformed in NEB5-α competent cells and sequences were verified ahead of transient transfection. In order to get dimeric IgA (dIgA), the heavy and light chain vectors were co-transfected with pcDNA containing DNA for the connecting J-Chain using an ExpiCHO expression system (Life Technology). For secretory expression (i.e., sIgA expression), a pcDNA containing secretory component was added to the transfection reaction in a 1:1 ratio. Supernatant was run through a column of CaptoL resin to capture the light chains of antibodies (GE Life Sciences). Antibodies were dialyzed against phosphate buffered saline before moving into size exclusion chromatography to separate out the desired dimeric or secretory antibodies using a HiLoad 26/600 Superdex 200 μg size exclusion column (GE Healthcare Life Sciences). Desired fractions were pooled, concentrated and quality tested by SDS-PAGE and western blots (FIGS. 6A and 6B).

ELISA Assay

For binding activity of purified HuMAbs against CfaE, 96-well plates (Nunc) were coated overnight at 4° C. with 2 μg/mL of purified MBP-CfaE-N. Plates were blocked with 1% BSA+0.05% Tween 20 in PBS. Purified HuMabs were diluted in 1×PBS+0.1% Tween 20 and added to plates for 1 hour. Plates were stained with alkaline phosphatase-conjugated goat anti-human IgG Fcγ (Jackson ImmunoResearch Laboratories) (1:1,000) for 1 hour and developed using p-nitrophenyl phosphate (ThermoFisher Scientific). Absorbance at an OD of 405 nm was measured on an Emax precision plate reader (Molecular Devices).

SPR Analysis

Surface plasmon resonance (SPR) technology was used to assess the binding properties of the HuMAbs (Biacore T200 instrument; GE Healthcare). A total of 2,700 response units (RU) of anti-human IgG MAb (human antibody capture kit; GE Healthcare) was coupled to a CM5 sensor chip using standard amine coupling chemistry. In multi-cycle kinetics experiments, 25 to 100 RU of each anti-CfaE HuMAb was captured on the anti-human IgG Mab bound sensor chip. Various concentrations of soluble recombinant MBP-CfaE-N antigen ranging from 1.56 nM to 50 nM were injected over the chip surface at a flow rate of 30 μl/min. An association step of 60 s was followed by a dissociation step of 180 s, and the final dissociation step was 600 s. Regeneration of the sensor chip surface was accomplished using 3M $MgCl_2$. Experiments were performed at 25° C. Kinetic data were analyzed using Biacore T200 Evaluation (version 3.0) software and a 1:1 binding model. All chemicals for the Biacore experiment were purchased from GE Healthcare.

Flow Cytometry

Binding of the HuMAbs to the surface of live bacteria was measured by flow cytometry as described previously (Giutini et al., *Clin. Vaccine Immunol.* 23:698-706, 2016). H10407, which expresses the target CFA/I antigen, was used as the test strain. Briefly, bacteria were grown in CFA medium supplemented with 50 μM deferoxamine overnight at 37° C. with gentle shaking. To measure HuMAb binding, a fixed concentration of anti-CfaE HuMAb (10 μg/mL) or, as a negative control, 100 μg/mL of an irrelevant MAb, was incubated with 107 bacteria/mL. Bound antibody was detected using CF488-conjugated goat anti-human IgG (Biotium).

Mannose-Resistant Hemagglutination (MRHA) Assay of Human Group a Erythrocytes

ETEC cultures were taken from frozen cell banks and diluted in sterile 0.15 M saline solution until reaching an $OD_{600\ nm}$ of 1 for the assay. Human erythrocytes type A+ stored in K3-EDTA were washed three times with 0.15 M saline solution and resuspended in the same solution to a final concentration of 1.5% (vol/vol). In a U-bottom 96-well plate (Nunc Thermo Scientific) 100 μl of HuMAb was added in duplicate to the top row and diluted 1:2 down the plate in 0.15 M saline solution. 50 μl of appropriately diluted ETEC was added to each well together with 50 μl of 0.1 M D-mannose solution (Sigma). The plate was incubated for 10 minutes at room temperature. After incubation, 50 μl of blood solution was added to the plate and mixed well (200 μl final volume). Plates were allowed to sit stagnant at 4° C. for two hours. Hemagglutination was then observed without the aid of magnification. The absence of a pellet of red blood cells at the bottom of the well is indicative of positive hemagglutination. Blood was ordered fresh every week (BioreclamationIVT).

Caco-2 Adhesion Assay

Caco-2 cells seeded at $1\times10^5$ cells/mL were grown in 24-well tissue culture plates containing Dulbecco's modified Eagle's medium (DMEM), at 37° C. in 5% $CO_2$ static. Frozen bacterial banks were streaked on CFA agar plates and grown overnight at 37° C. The next day, bacteria were resuspended in PBS and diluted until reaching an $OD_{600\ nm}$ of 0.1. HuMab dilutions were set up in a deep well plate. Antibody dilutions and bacteria were combined in a 1:10 ratio and allowed to shake at 300 rpm for one hour at room temperature. After incubation, 0.2 mL of antibody/bacteria mixture was added to each well containing Caco-2 cells. The cells were then incubated statically for 3 hours at 37° C. Cells were then washed four times with 1 mL PBS to remove non-adherent ETEC cells. Afterwards, Caco-2 cells were dislodged with 0.2 mL 0.25% trypsin. Cells were collected via gentle centrifugation and resuspended in 1 mL of PBS. Dilutions were plated on CFA agar plates and colonies counted the next day. $IC_{50}$ was defined as concentration of HuMAb needed to inhibit 50% of ETEC adhesion to the Caco-2 cells, compared to an irrelevant isotype antibody.

Animal Assays

Six- to eight-week-old DBA-2 mice were pretreated with streptomycin (5 g/L) in the drinking water for 24-48 hours. Twelve hours prior to bacteria administration the water was replaced with regular drinking water. One hour prior to bacteria administration, mice received cimetidine (50 mg/kg) i.p. to reduce the effect of stomach acid on ETEC. A total of $10^7$ CFU of H10407 ETEC strain diluted in PBS were incubated with 10 mg/kg of an anti-CfaE HuMAb or an irrelevant MAb (purified human secretory IgA, MP Biomedicals) one hour prior challenge. Bacteria and HuMAbs were administered in 200 μl volume by oral gavage using 20 g bulb-tip feeding needles. The mice were allowed to survive for 24 hours. 12 hours prior to euthanasia, food was withdrawn. Following isolation of the small intestine, two segments of ileum (3 cm each), beginning within 0.5 cm of the ileocecal junction and extending proximally 6 cm, were removed and placed in 1 mL of sterile PBS (Allen et al., Infect. Immun. 74:869-75, 2006). Tissues were mechanically homogenized. Samples were serially diluted on MacConkey agar plates and incubated overnight at 37° C. Bacterial CFUs were counted the next day. To confirm that recovered bacteria were the inoculum strain, bacterial colonies grown on culture plates were routinely tested by PCR using specific primers (Allen et al., Infect. Immun. 74:869-75, 2006), which flank the eltAB operon encoding the LT holotoxin of H10407.

Epitope Mapping

Bioluminate software (Schrödinger) was used to identify CfaE residues involved in antibody-antigen recognition. A total of 22 amino acids predicted by the software to be involved in the interaction between anti-CfaE HuMAbs and the N-terminal portion of CfaE were individually mutated to Alanine using BioXp™ 3200 System (SGI-DNA). The genes were cloned into pMAL-C5x vector and the resulting 22 constructs were transformed, expressed and purified as described above. An ELISA assay was performed to determine binding of the HuMAbs to the mutant proteins compared to the wild-type.

Statistical Analysis

Statistical calculations were performed using the software Prism version 7.03 (GraphPad Software, La Jolla, CA). Comparisons between the hemagglutination or Caco-2 titers of respective antibodies were performed using multiple comparisons, Bonferroni test, one way ANOVA.

Example 2. Generation of Anti-CfaE HuMabs

The N-terminal portion of the adhesin CfaE acts as the receptor binding domain of CFA/I adhesion to host cells (Li et al., J. Biol. Chem. 282:23970-80, 2007). To generate a panel of HuMabs that can provide anti-adhesive immunity, eight mice transgenic for human immunoglobulin heavy and light chain genes (Bristol-Myers Squibb; HuMab mice) were immunized with the N-terminal adhesin domain of CfaE fused to maltose-binding protein (MBP-CfaE-N). Serum response to MBP-CfaE-N was measured by ELISA. Spleens from mice with positive ELISA response were harvested and fused to melanoma cells to generate hybridomas. A total of 1895 hybridomas were found reactive to MBP-CfaE-N but not the MBP tag itself. RT-PCR was performed on 900 hybridomas to determine the antibody heavy chain gene sequences. A total of 360 HuMabs with unique sequences were selected for further characterization.

Example 3. Selection of Ten Lead HuMabs in Mannose Resistant Hemagglutination Assays All 360 unique HuMabs were purified and tested for their ability to inhibit mannose resistant hemagglutination of human group A erythrocytes (MRHA). MRHA has long been considered as a surrogate method for assessment of ETEC adhesion to the intestinal mucosa (Hagberg et al., Infect. Immun. 31:564-570, 1981). The results of the MHRA assays were reported as the maximal inhibitory concentration ($IC_{100}$). 36 of all 360 HuMabs showed $IC_{100}$ activity in nanomolar concentration range. Ten HuMabs were selected with the $IC_{100}$ values between 0.13 μg/mL and 0.24 μg/mL. The heavy chain and light chain gene regions of the selected HuMabs were amplified from hybridoma cells and cloned into an immunoglobulin G1 expression vector for antibody expression and purification as previously described. Heavy and light variable gene families of the selected HuMabs are reported in Table 2.

TABLE 2

Anti-CfaE HuMAb heavy and light chain variable gene families

| | Heavy chain sequence | | | Light chain sequence | |
|---|---|---|---|---|---|
| clone # | Vh | D | Jh | Vl | Jk |
| 68-51 | 4-34 | 2-08 | 3 | 1-12 | 2 |
| 68-61 | 1-69 | 2-21 | 3 | 1-16 | 2 |
| 68-97 | 4-34 | 7-27 | 3 | 1-12 | 2 |
| 68-90 | 4-34 | 7-27 | 3 | 1-12 | 2 |
| 68-75 | 4-34 | 2-02 | 6 | 1-13 | 1 |
| 67-102 | 4-34 | 2-15 | 3 | 1-12 | 4 |
| 840-53 | 30-30 | 7-27 | 4b | 1-06 | 1 |
| 68-48 | 4-34 | 7-27 | 6 | 1-13 | 1 |
| 837-6 | 3-23 | 6-06 | 2 | 1-27 | 5 |
| 68-06 | 1-69 | 4-17 | 3 | 1-16 | 2 |

Example 4. Anti-CfaE HuMabs Bind to Recombinant CfaE and Live ETEC Strain

Figure 1B:
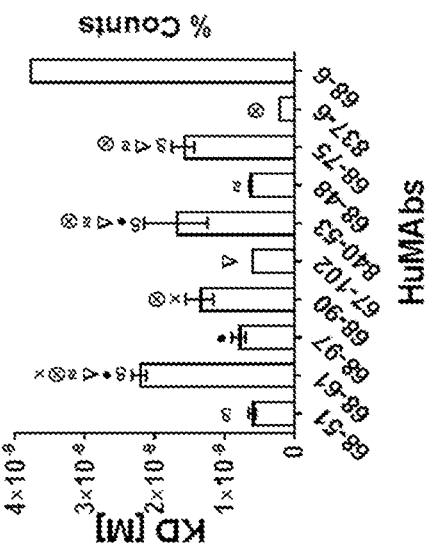
FIG. 1B is a graph showing equilibrium dissociation constant ($K_D$) as measured by surface plasmon resonance. Error bars represent the standard deviation in two independent experiments. All the anti-CfaE antibodies were significantly different compared to antibody 68-6 (P<0.0001). Symbols represent significant differences (P<0.01) between the anti-CfaE antibodies using one way ANOVA.

ELISA results showed that the concentration-dependent binding to CfaE by the HuMAbs was indistinguishable (FIG. 1A). To further differentiate the CfaE-binding activities of HuMabs, antibody affinity was analyzed by surface plasmon resonance using recombinant MBP-CfaE-N. All ten HuMabs showed high affinities to MBP-CfaE-N with dissociation constant ($K_D$) values in the low nanomolar range (0.6 nM to 1.2 nM) (FIG. 1B). HuMab 837-6 showed the highest affinity of the ten with a $K_D$ value of $2.3 \times 10^{-10}$. HuMab 68-51, 68-97, 67-102, 68-48, and 837-6 were found to have higher affinity as compared to HuMab 68-61, 68-90, 840-53, and 68-75.

Figure 1C:
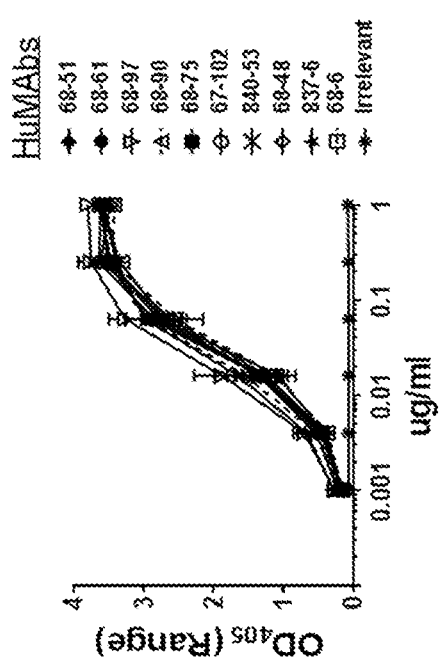
FIG. 1C is a graph showing direct binding activity of antibodies to live bacterial cells (H10407 strain) measured by flow cytometry. Gray filled area represents bacteria incubated with an irrelevant antibody.

To assess HuMab recognition of CfaE expressed by live bacteria, H10407 strain was grown in an iron starvation condition to induce CfaE protein expression (Haines et al., J. Bacteriol. 197:2896-907, 2015). The bacteria was then incubated with each of the ten selected HuMabs, followed by fluorescence-conjugated secondary antibody and FACS analysis. All HuMabs showed strong binding activity to the H10407 strains. The binding activities were comparable among all ten antibodies (FIG. 1C).

Figure 2A:
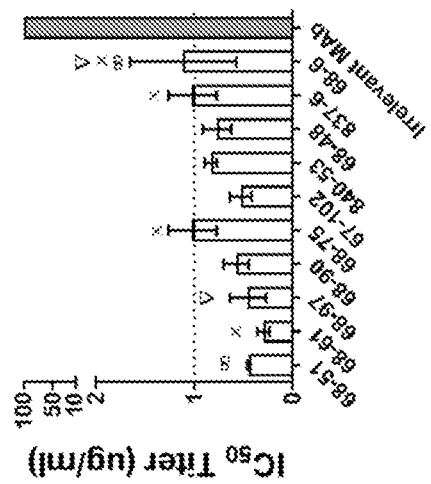
FIG. 2A is a graph showing in vitro functional activity of the anti-CfaE antibodies measured via a mannose-resistant hemagglutination (MRHA) assay. The ability of the antibodies to prevent hemagglutination is reported as maximal inhibitory concentration ($IC_{100}$). Error bars represent the standard deviation observed in three independent experiments using different blood donors.
Figure 2B:
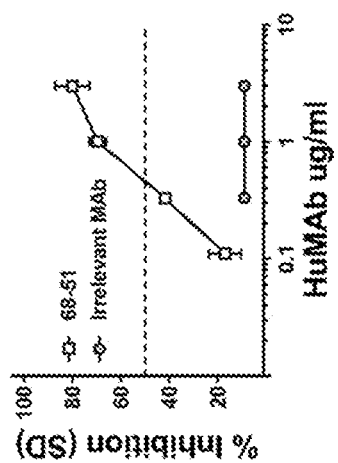
FIG. 2B is a graph showing in vitro functional activity of the anti-CfaE antibodies measured via a Caco-2 adhesion assay. Example of inhibition curve obtained with antibody 68-51 and an irrelevant control.
Figure 2C:
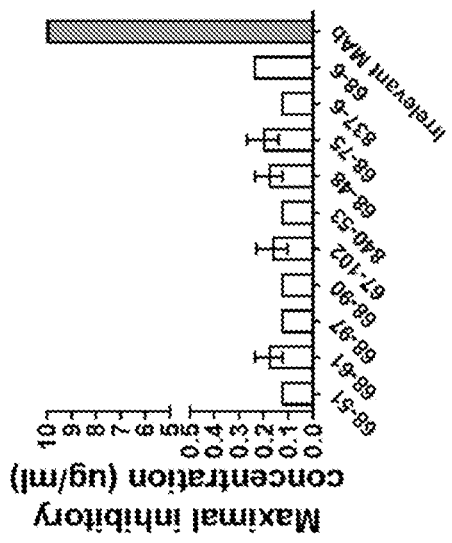
FIG. 2C is a graph showing the minimal effective IgG dose of anti-CfaE antibodies to prevent 50% ($IC_{50}$) of bacterial adhesion to intestinal Caco-2 cells. $IC_{50}$ was used to determine antibody potency ranking. Error bars represent the standard deviation in three to four independent experiments. All the anti-CfaE antibodies were significantly different compared to the irrelevant antibody (P<0.0001). Symbols represent significant differences (P<0.01) within the anti-CfaE antibodies using one way ANOVA.

Example 5. Anti-CfaE HuMabs Prevent ETEC Adherence to Intestinal Cells at Low Concentrations To determine whether the lead HuMabs were capable of inhibiting bacterial adhesion, a cell adhesion assay with Caco-2 cells (a human intestinal epithelial cell line) was performed. An example of concentration-dependent inhibition curve is reported in FIG. 2B. The minimal inhibitory concentrations needed to prevent 50% ($IC_{50}$) of bacterial adhesion were reported as antibody potency. All ten HuMabs showed strong potency to block bacteria adhesion at $IC_{50}$ concentrations between 0.3 to 1.3 µg/mL. HuMab 68-51, 68-61, and 68-97 were found to have the lowest $IC_{50}$ values (FIG. 2C). Interestingly, HuMabs showing comparable activities in MRHA assays (FIG. 2A) were more variable in their activities in Caco-2 cell adhesion assays.

Example 6. Epitope Mapping of Anti-CfaE HuMabs

Figure 3G:
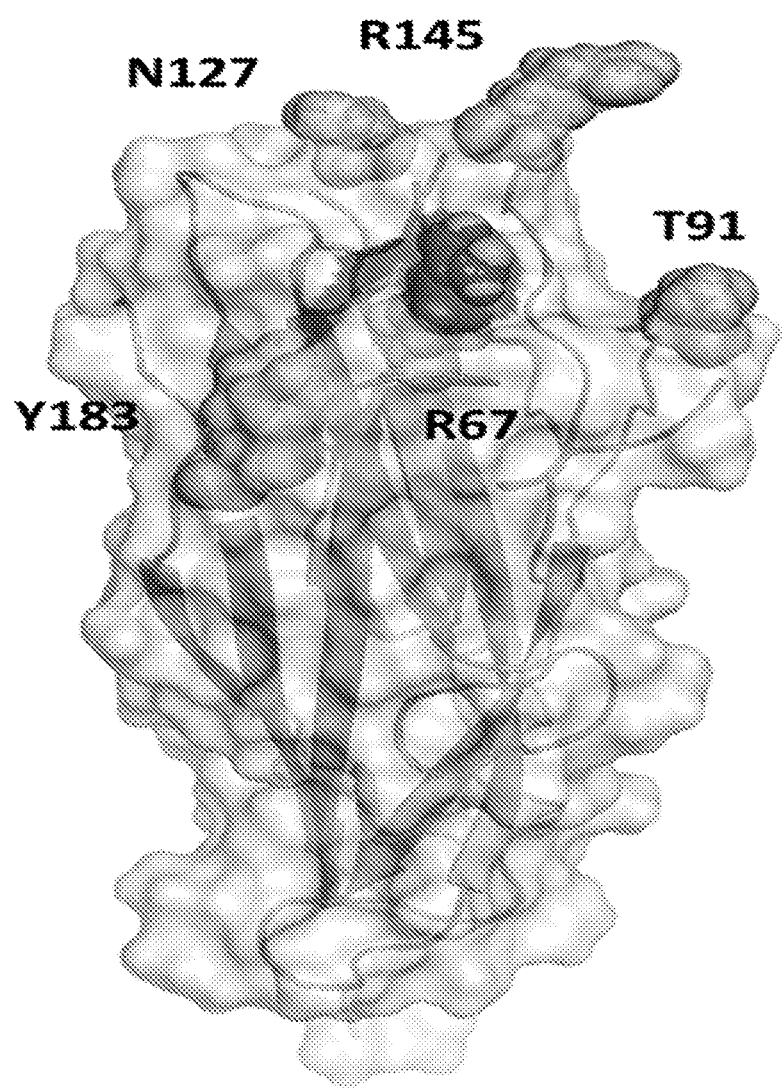
FIG. 3G is a rendering of the crystal structure of the N-terminal CfaE molecule with the five residues involved in the anti-CfaE antibodies binding showed as green spheres. The three arginines forming the putative receptor binding domain are highlighted in red.

To define the antibody-binding epitope, putative antibody-antigen interaction models were established based on a previously resolved CfaE structure (PDB ID 2Hb0) and the HuMab antibody sequences using an antibody modeling program, BioLuminate (Schrodinger). This software suite develops models of antibody structures from their sequences, followed by computational docking to identify high-confidence antibody-antigen complex models. Based on these models, the software identified potential residues critical for binding interaction. The effect of these residues on the binding activity of the HuMAbs was analyzed by experimental alanine scanning followed by ELISA. ELISA results indicated that mutating five of the predicted residues to alanine affected HuMAb binding (FIGS. 3A-3G). The R67A mutation eliminated binding activity of HuMab 68-51 and 68-97 (FIG. 3B), while the Y183A mutation affected binding activity of HuMab 68-51, 68-97, 68-90, 67-102, and 840-53 (FIG. 3E). R145A mutation abolished binding activity of HuMab 837-5 (FIG. 3D). T91A mutation eliminated binding activity of HuMAb 840-53 and reduced binding activities of HuMAbs 68-51, 68-61, 840-53 and 68-48 (FIG. 3C). N127A mutation eliminated binding activity of HuMAb 68-61 and reduced binding of HuMAbs 68-48 and 68-6 (FIG. 3F). Summary of the residues discovered to affect binding are shown in Table 3. All mutations were found on the surface exposed loops of the N-terminal domain of the CfaE (FIG. 3G). No residues involved in the binding of MAb 68-75 to CfaE were identified.

TABLE 3

Summary of residues affecting binding of MAbs to CfaE

| MAb | Amino acid binding residues on CfaE | | | | |
|---|---|---|---|---|---|
| | R67 | R145 | Y183 | T91 | N127 |
| 068-51 | x | | x | x | |
| 068-61 | | | | | x |
| 068-97 | x | | x | x | |
| 068-90 | | | x | | |
| 068-75 | | | | | |
| 067-102 | | | x | x | |
| 840-53 | | | x | x | |
| 068-48 | | | | x | x |
| 837-6 | | x | | | |
| 068-6 | | | | | x |

Example 7. Isotype Switch of Anti-CfaE HuMabs to sigA

Figure 4:
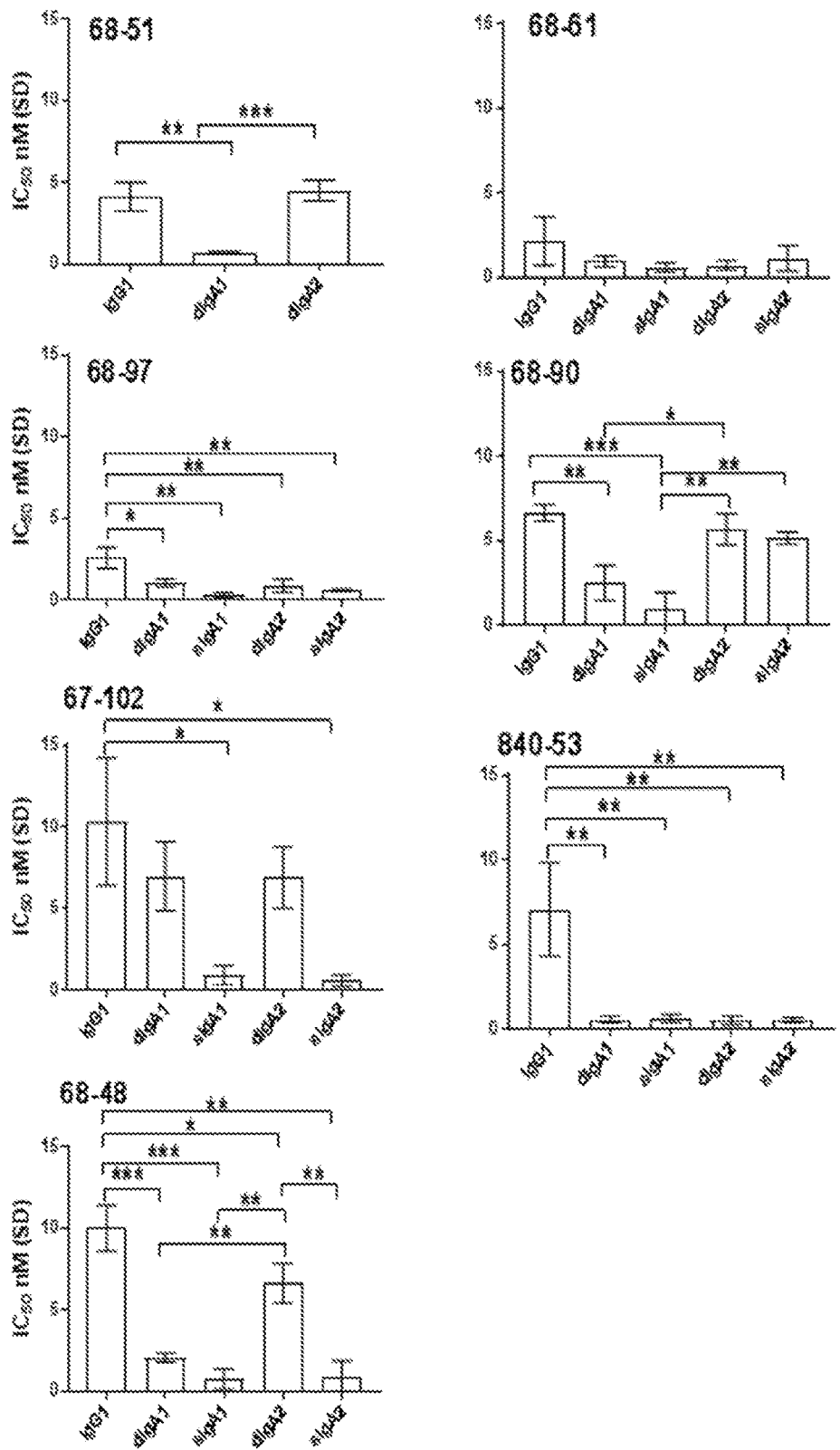
FIG. 4 is a series of graphs showing anti-CfaE antibody activity after Ig class switching measured via Caco-2 adhesion assay. The minimal effective IgG dose to prevent 50% ($IC_{50}$) of bacterial adhesion to intestinal Caco-2 cells was used to determine antibody potency ranking. Error bars represent the standard deviation in three to four independent experiments. *P<0.01, P<0.001, *P<0.0001.

Seven IgG1 HuMabs (68-51, 68-61, 68-97, 68-90, 67-102, 68-48, and 840-53) found to have the lowest $IC_{50}$ values in Caco-2 cell adhesion assays were selected for further characterization in immunoglobulin class switching. Antibody variable regions were cloned into an expression vector with IgA constant region to generate monomeric IgA. Monomeric IgA antibodies were also co-expressed with J chain with or without secretory component to produce secretory (sIgA) and dimeric IgA (dIgA), respectively. Antibodies with various isotypes were tested for their functionality in Caco-2 cell adhesion assays (FIG. 4). In general, all the antibodies retained or increased in vitro functional activity when converted into dIgA or sIgA. Specifically, in vitro functional activity of 68-61 was not altered significantly when converted to either dimeric or secretory IgA molecule. In contrast, Ig class switching to either dimeric or secretory IgA forms caused significant improvement of functional activity for HuMAbs 68-97, 840-53, and 68-48. Interestingly, HuMAb 68-90 only saw a significant improvement when Ig class switch to dimeric or secretory IgA1. Additionally, conversion from an IgG1 to a dimeric IgA1 or IgA2 did not affect functional activity of HuMAb 67-102, but switching from dimeric to secretory IgA1 or IgA2 did significantly increase in vitro activity of 67-102. Due to low expression yields, sufficient amounts of 68-51 sIgA1 or sIgA2 could not be generated for in vitro testing.

Figure 5:
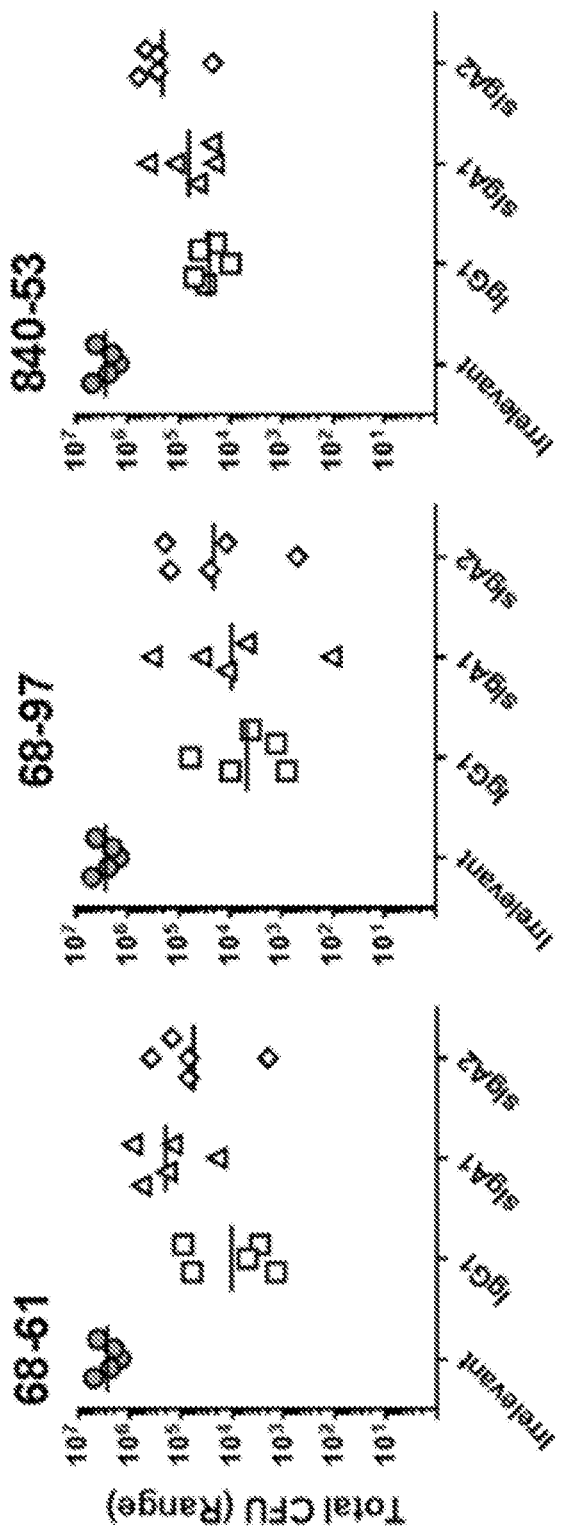
FIG. 5 is a series of graphs showing in vivo functional activity of the identified anti-CfaE antibodies. DBA/2 mice were challenged intragastrically with 107 CFU pre-incubated with 10 mg/kg of antibodies. Animals were euthanized 24 hours after challenge and bacterial colonies in the small intestine were counted. Five animals were tested for each condition. All the anti-CfaE antibodies were significantly different compared to the irrelevant antibody (P<0.001).

Example 8. Anti-CfaE HuMabs Prevent ETEC Colonization in the Small Intestine of a Mouse Model HuMAbs 68-61, 68-97, and 840-53 were found to have the lowest $IC_{50}$ values as IgG1, sIgA1, and sIgA2 and were selected as the leads for further characterization in animal studies (FIG. 5). Groups of five DBA2 mice were given a mixture of bacteria and anti-CfaE HuMAbs (10 mg/kg) by oral gavage. 24 hours after challenge, the mice were euthanized and the CFU in the small intestine were counted as described in the methods. The efficacy of the anti-CfaE HuMAbs was assessed by determining whether the HuMAbs could prevent adhesion of bacteria to the small intestine compared to an irrelevant isotype control. In the 68-61 group, treatment with IgG1 decreased CFU by 100 fold compared to the irrelevant antibody control. A similar result was observed for 68-61 sIgA2 and sIgA1 compared to the irrelevant control. The reduction of CFU observed in the 68-97 group compared to the irrelevant control was similar across the different subclasses. In the 840-53 group, mice treated with IgG1 showed less bacteria compared to sIgA2, while sIgA1 also showed a decrease in bacteria relative to sIgA2, though these differences were not significant.

Figure 7:
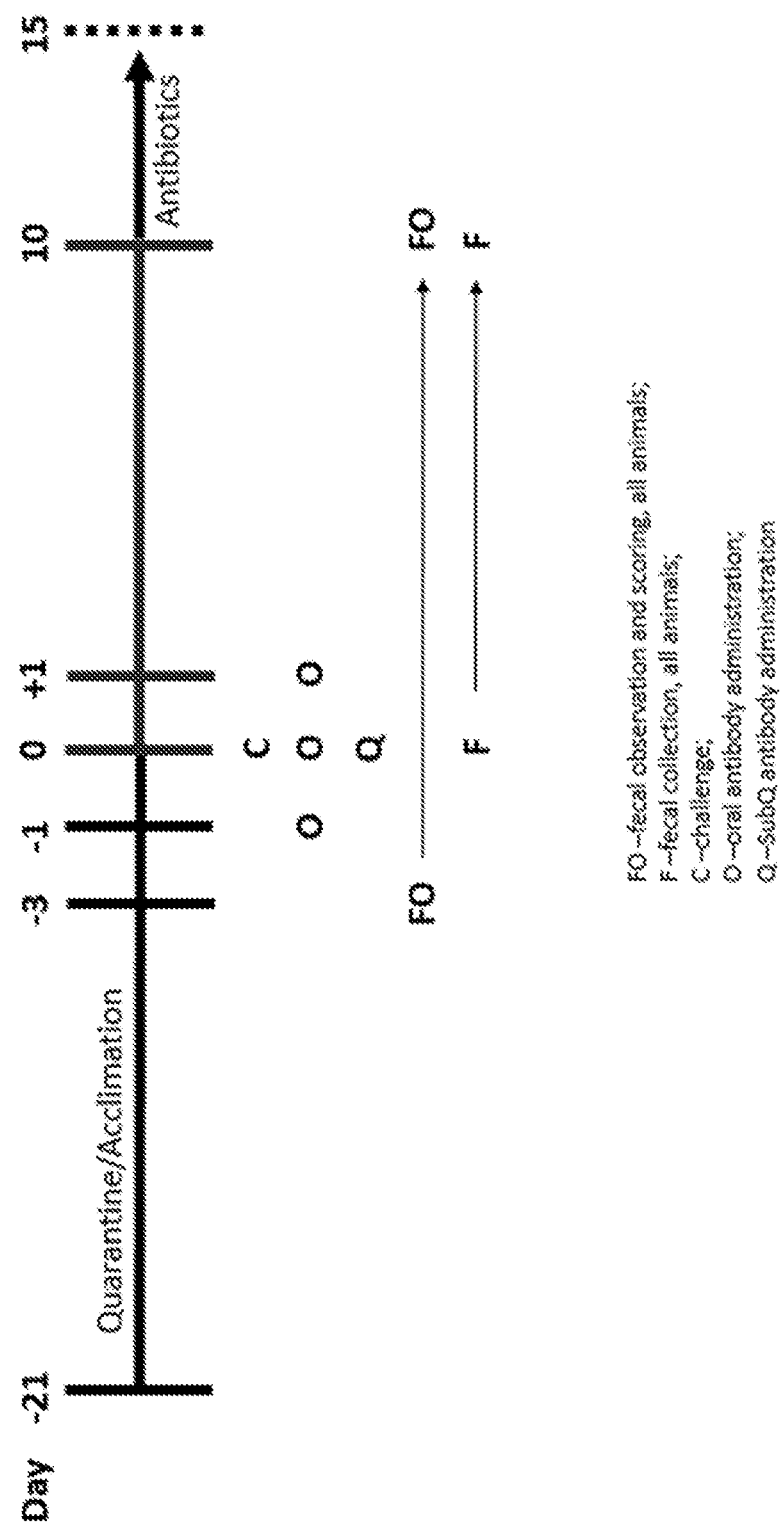
FIG. 7 is a timeline of the study design of the challenge experiment. FO=fecal observation and scoring, all animals.

Example 9. Oral Administration of Anti-CfaE Secretory IgA (sigA) Antibody Protects Against ETEC in Non-Human Primate Model The efficacy of anti-CfaE sIgA, 68-61, was evaluated in an *Aotus nancymaae* non-human primate ETEC challenge model (ETEC strain H10407). In this model, *Aotus nancymaae* has been shown to be susceptible to diarrhea in response to experimental infection with ETEC expressing CFA/I, mimicking ETEC pathogenesis in humans. Anti CfaE antibody 68-61 was administered to *Aotus* either as a dimeric IgA2 (dIgA2) via a single subcutaneous dose (SC) on the day of challenge (day 0) or as a secretory IgA2 (sIgA2) via oral delivery on days −1, 0 (challenge day), and +1 (FIG. 7). Animals were then monitored for diarrhea as previously described.

Production and Characterization of 68-61 sIgA2 and dIgA2 Antibodies for NHP Studies Large scale production for anti-CfaE 68-61 dIgA2 and sIgA2 antibodies were set up to generate sufficient material for NHP studies using an established IgA production platform (Giuntini, S., et al. (2018) Infect. Immun. Vol. 86; e00355-18). To generate dIgA2, the heavy and light chain vectors were co-transfected with a J chain-expressing vector with equal molar ratio in CHO cells. For sIgA2, a secretory component-expressing vector was added to the dIgA2 transfection reaction (equal molar ratio for all vectors). Supernatant was run through a column of Capture Select IgA (ThermoFisher) or CaptoL resin (GE Life Sciences) for dIgA and sIgA respectively, followed by size exclusion chromatography (HiLoad 26/600 Superdex 200 µg size exclusion column; GE Life Sciences) to separate out the desired dimeric or secretory antibodies. To verify the antibody quality, purified antibodies were analyzed by SDS-PAGE and western blots (FIG. 8A). MRHA and Caco-2 cell adhesion assays were also conducted to test the antibody in vitro functionalities. Similar to what was reported previously, both purified 68-61 dIgA2 and sIgA2 showed functional activity in both hemagglutination assay (minimal inhibitory concentration of 0.04 µg/ml and 0.08 µg/ml) and Caco-2 adhesion assay (FIGS. 8B and 8C, respectively).

Administration of Antibody and ETEC Challenge Inoculums

The ETEC challenge model has been previously described (Giuntini, S., et al. (2018) Infect. Immun. Vol. 86; e00355-18; Rollenhagen, J. E., et al. (2019), Infect. Immun. Vol. 87: e00634-18). Briefly, *Aotus nancymaae* monkeys were screened by enzyme-linked immunosorbent assay (ELISA). Animals deemed seropositive were excluded from the study. The remaining thirty-nine animals were distributed across three groups of 13 according to age, sex, and weight. Following a 21-day acclimation period, the animals were fasted overnight and on study day 0 all animals were anesthetized with ketamine hydrochloride (10 mg/kg weight, Ketalar, Parke-Davis) and an orogastric feeding tube was placed (5Fr/Ch, 1.7 mm×41 cm). All animals also received ranitidine (1.5 mg/kg) by intramuscular injection 90 minutes prior to challenge to inhibit gastric acid production, and 5 ml CeraVacxII (CeraProducts, Jessup, MD) was given 30 minutes prior to challenge to neutralize stomach pH. All animals were then challenged with $5 \times 10^{11}$ cfu ETEC CFA/I$^+$ H10407 (5 ml volume).

All groups received an antibody treatment (9 mg/kg) prior to challenge on Day 0. Group 1 received an anti-CfaE dIgA2 antibody by subcutaneous (SC) injection. Group 2 received an anti-CfaE sIgA2 antibody via the orogastric line. Group 3 received a control sIgA2 antibody against an HIV target (no cross-reactivity with H10407 in vitro) via the orogastric line. Group 2 and Group 3 also received antibody treatment one day prior to challenge (day −1) and one day post challenge (day+1). These additional treatments (9 mg/kg) were prepared by diluting the antibody (anti-CfaE sIgA2 for Group 2 and control sIgA2 for Group 3) into 5 mL total volume of Prang oral rehydration drink (Bio-Serv; orange flavor), and the diluted antibody was then administered orally by syringe via voluntary consumption. All animals were observed for 10 days and then treated with enrofloxacin until ETEC H10407 was not detected in stool samples. The study design of the ETEC challenge model is illustrated in FIG. 7. The demographic variables of animals in each individual group are listed in Table 4.

Observation after Passive Immunoprophylaxis and Challenge

Animals were observed twice daily for signs and symptoms of diarrhea starting on study day −3 and continuing for 10 days after challenge. Stools were graded as follows: grade 1 (formed, firm stool pellets), grade 2 (formed but soft stool pellets or droppings), grade 3 (loose, unformed feces), grade 4 (watery, non-clear feces), and grade 5 (watery, clear liquid stools). Stools graded 1 or 2 were considered normal, whereas stools graded 3, 4, or 5 were considered abnormal. The case definition of a diarrhea episode was defined as the passing of grade 3 or higher stools for at least two consecutive days during the observation period. The duration of diarrhea was defined as the time between the first day of a diarrhea episode and the last day of diarrhea preceding two consecutive diarrhea-free days. Animals meeting the case definition of diarrhea prior to the challenge were excluded from data analysis.

Fecal cultures for H10407 ETEC were performed daily for 10 days after challenge by streaking fresh stool and plating serial dilutions of stool directly onto MacConkey agar. Presumptive H10407 isolates (lactose-positive) were confirmed by colony blot using rabbit antisera against CFA/I. Stool was considered negative for H10407 if no lactose-positive *E. coli* colonies were isolated, or if 10 presumptive colonies were negative by immunoblot. A period of fecal shedding was defined as isolation of H10407 (CFA/I positive colonies) from stool collected after challenge, beginning (onset) as early as the first day after challenge and ending (duration) on the last day that H10407 is detectable in stool, up to day 10 post challenge.

Statistical Analyses

Intergroup comparisons of clinical outcomes were performed using nonparametric tests for continuous outcomes (Kruskal-Wallis test for comparing the values for more than two groups) and Fisher's exact test for nominal outcomes. All statistical tests were interpreted in a two-tailed fashion with acceptance of significance set at the $P<0.05$ level.

Antibody Efficacy Study in a Non-Human Primate Model Challenged with ETEC

Dimeric (Group 1) and secretory (Group 2) anti-CfaE IgA2 antibodies were administered to *A. nancymaae* monkeys, as described above, to determine their efficacy against ETEC H10407 strain. Animals administered the irrelevant control sIgA2 antibody (Group 3, oral) had a diarrheal attack rate of 58% (7/12), within the range of the reported attack rate in this animal model (Rollenhagen, J. E., et al. (2019), Infect. Immun. Vol. 87: e00634-18). Anti-CfaE dIgA2 treatment (Group 1; SC) lowered the attack rate to 23% (3/13), while sIgA2 treatment (Group 2; oral) significantly lowered the attack rate to 15% (2/13) as compared to Group 3. One animal in Group 3 was excluded from analysis due to the onset of diarrhea prior to challenge (Table 4). There was no significant difference in the colonization rate or the duration of shedding between the treatment groups (Table 5).

TABLE 4

Demographic variable and study design

| | | | | | | Study design | | | |
|---|---|---|---|---|---|---|---|---|---|
| Group | Treatment | N° of animals | N° males/ females | Mean age, months (SD) | Mean weight, grams, (SD) | Route | Dose | Time points of administration | Challenge day |
| 1 | dIgA2 anti-CfaE | 13 | 6/7 | 16.1 (1.38) | 853.5 (111.5) | Sub-Q | 9 mg/Kg | SD 0 | SD 0 |
| 2 | sIgA2 anti-CfaE | 13 | 7/6 | 15.9 (1.32) | 819 (42.6) | Oral-OG | 9 mg/Kg | SD-1, 0, 1 | SD 0 |
| 3 | Control IgA2 | 12[a] | 7/6 | 16.1 (1.28) | 812.5 (72.3) | Oral-OG | 9 mg/Kg | SD-1, 0, 1 | SD 0 |

[a]One animal excluded from data analysis due to diarrhea for 3 days prior to challenge

TABLE 5

Diarrhea and colonization after oral challenge

| | | | Diarrhea[a] | | | Fecal Shedding[b] | | |
|---|---|---|---|---|---|---|---|---|
| Treatment | No. of animals | No. of cases | Incidence (%) | Mean no. of days to onset (range) | Mean no. of days to illness (range) | Incidence (%) | Median no. of days to onset | Median no. of days of duration (range) |
| dIgA2 anti-CfaE | 13 | 3 | 23 | 4 (1-9) | 2.3 (2-3) | 100 | 1 | 6.3 (3-9) |
| sIgA2 anti-CfaE | 13 | 2 | 15 | 4 (1-7) | 3 (2-4) | 100 | 1 | 7 (5-10) |
| Control IgA2 | 12[c] | 7 | 58 | 1.8 (1-7) | 3.1 (2-6) | 100 | 1 | 7.3 (3-10) |

[a]Diarrhea defined as at least one loose-watery stool on at least two consecutive days during the observation period (10 days) post challenge.
[b]Fecal shedding assessed by plating on MacConkey agar with confirmatory colony blotting.
[c]One animal excluded from data analysis due to diarrhea for 3 days prior to challenge.

Based on the diarrheal attack rates, oral anti-CfaE sIgA2 (Group 2) treatment resulted in a protective efficacy of 71.4% (P=0.025) compared to the irrelevant sIgA2 (Group 3). Treatment with a subcutaneous injection of anti-CfaE dIgA2 (Group 1) reduced the diarrheal attack rate, although the reduction did not reach significance (57.1%; P=0.072) as compared to Group 3 (Table 6). Of note, Group 1 animals did not receive any of the oral rehydration drink on days −1 and +1 that was used to orally administer the sIgA antibodies in Groups 2 and 3.

While both IgG and IgA are expressed at the mucosa, IgA is usually more effective on a molar basis and thus are the natural choice for mucosal passive immunization. The avidity of mucosal IgA, due to multimeric structure, enhances antibody binding with antigens and increases antibody mediated conformational or structural changes in the antigen. The diverse, high level of glycosylation of IgA antibodies, in comparison to IgG, further protects the mucosal surface by non-specific interference with microbial adherence. Therefore, the feasibility of administration of anti-CfaE IgA for protection against an ETEC challenge in the A. nancymaae non-human primate model was explored.

Oral delivery of an anti-CfaE sIgA2 resulted in 71.4% protective efficacy against ETEC diarrhea in animals (Table 6). The administration of a single dose of anti-CfaE dIgA antibody subcutaneously resulted in a 57.1% reduction of ETEC diarrhea (Table 6). Though not significant (P=0.072), in contrast to the control animals (Group 3), Group 1 animals did not receive any of the oral rehydration drink, which may have imparted a small therapeutic effect to the control animals not recapitulated in Group 1 (Table 6). Eliminating this difference, dose optimization, and/or temporal administration experiments may reveal a significant reduction in diarrhea and further experimentation is clearly warranted.

TABLE 6

Protective Efficacy in A. nancymaae

| Group | Vaccine | No. with diarrhea/N (%) | Protective Efficacy % | P value[a] |
|---|---|---|---|---|
| 1 | Dimeric anti-CfaE IgA2 | 3/13 (23) | 57.1 | 0.072 |
| 2 | Secretory anti-CfaE IgA2 | 2/13 (15) | 71.4 | 0.025 |
| 3 | Control IgA2 | 7/12 (58) | — | |

[a]Fisher Exact Test, two-tailed, comparing frequency of diarrhea test groups to control group.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that specifically binds CfaE, wherein the antibody comprises the following CDRs:
   (a) a CDR-H1 comprising the amino acid sequence of GGSFSAYYWS (SEQ ID NO: 33);
   (b) a CDR-H2 comprising the amino acid sequence of EINHSGNTNYNPSLES (SEQ ID NO: 34);
   (c) a CDR-H3 comprising the amino acid sequence of ARNWGPNAFDI (SEQ ID NO: 35);
   (d) a CDR-L1 comprising the amino acid sequence of QDITSW (SEQ ID NO: 36);
   (e) a CDR-L2 comprising the amino acid sequence of AAS (SEQ ID NO: 37); and
   (f) a CDR-L3 comprising the amino acid sequence of QQANIFPYT (SEQ ID NO: 38).

2. The antibody of claim 1, wherein the antibody comprises a VH domain comprising an amino acid sequence having at least 95% sequence identity to the amino acid sequence of SEQ ID NO: 47 and a VL domain comprising an amino acid sequence having at least 95% sequence identity to the amino acid sequence of SEQ ID NO: 48.

3. The antibody of claim 1, wherein the antibody is a monoclonal antibody or a human antibody.

4. The antibody of claim 1, wherein the antibody is an IgG class antibody or an IgA class antibody.

5. The antibody of claim 4, wherein the IgA class antibody is a secretory IgA (sIgA) class antibody or a dimeric IgA (dIgA) class antibody.

6. The antibody of claim 1, wherein the antibody is a full-length antibody.

7. The antibody of claim 1, wherein the antibody is an antibody fragment that specifically binds CfaE selected from the group consisting of Fab, Fab', Fab'-SH, Fv, single chain variable fragment (scFv), and (Fab')$_2$ fragments.

8. The antibody of claim 1, wherein the antibody is capable of inhibiting mannose-resistant hemagglutination of human group A erythrocytes with a maximal inhibitory concentration (IC$_{100}$) of between about 0.10 μg/mL and about 0.25 μg/mL.

9. The antibody of claim 1, wherein the antibody specifically binds CfaE expressed on the surface of a live enterotoxigenic *Escherichia coli* (ETEC) strain with a K$_D$ of between about 0.1 nM and about 10 nM.

10. The antibody of claim 1, wherein the antibody is capable of inhibiting the binding of ETEC bacteria to intestinal cells with a 50% inhibitory concentration (IC$_{50}$) of between about 0.10 μg/mL and about 10 μg/mL.

11. A composition or a pharmaceutical composition comprising the antibody of claim 1.

* * * * *

SEQUENCE LISTING

<160> NUMBER OF SEQ ID NOS: 48

<210> SEQ ID NO 1
<211> LENGTH: 10
<212> TYPE: PRT

<213> ORGANISM: Artificial Sequence
<220> FEATURE:
<223> OTHER INFORMATION: Synthetic Construct

<400> SEQUENCE: 1

Gly Gly Thr Phe Ser Ser Phe Ala Ile Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Arg Ile Ile Pro Ile Leu Asp Ile Val Lys Tyr Ala Gln Arg Phe Gln
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Ala Arg Asp Asp Ile Ala Gly Ser Asp Phe Asp Ile
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Gln Gly Ile Ser Ser Trp
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic Construct

<400> SEQUENCE: 5

Ala Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Tyr Thr Ser Tyr Pro Tyr Thr
1               5

<210> SEQ ID NO 7
<211> LENGTH: 25

```
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Gln Ser Gly Ala Glu Val Lys Asn Pro Gly Ser
1               5                   10                  15

Ser Val Arg Val Ser Cys Glu Ala Ser
            20                  25

<210> SEQ ID NO 8
<211> LENGTH: 14
<212> TYPE: PRT
<213> ORGANISM: Artificial Sequence
<220> FEATURE:
<223> OTHER INFORMATION: Synthetic Construct

<400> SEQUENCE: 8

Trp Val Arg Gln Ala Pro Gly Gln Gly Leu Glu Trp Met Gly
1               5                   10

<210> SEQ ID NO 9
<211> LENGTH: 30
<212> TYPE: PRT
<213> ORGANISM: Artificial Sequence
<220> FEATURE:
<223> OTHER INFORMATION: Synthetic Construct

<400> SEQUENCE: 9

Arg Val Thr Ile Ser Ala Asp Lys Ser Thr Ser Thr Ala Tyr Met Glu
1               5                   10                  15

Leu Ser Ser Leu Arg Ser Glu Gly Thr Ala Val Tyr Tyr Cys
            20                  25                  30

<210> SEQ ID NO 10
<211> LENGTH: 14
<212> TYPE: PRT
<213> ORGANISM: Artificial Sequence
<220> FEATURE:
<223> OTHER INFORMATION: Synthetic Construct

<400> SEQUENCE: 10

Trp Gly Gln Gly Thr Met Val Thr Val Ser Ser Ala Ser Thr
1               5                   10

<210> SEQ ID NO 11
<211> LENGTH: 26
<212> TYPE: PRT
<213> ORGANISM: Artificial Sequence
<220> FEATURE:
<223> OTHER INFORMATION: Synthetic Construct

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 12

Leu Ala Trp Tyr Gln Gln Lys Pro Glu Lys Ala Pro Lys Ser Leu Ile
1               5                   10                  15

Tyr

<210> SEQ ID NO 13
<211> LENGTH: 36
<212> TYPE: PRT
<213> ORGANISM: Artificial Sequence
<220> FEATURE:
<223> OTHER INFORMATION: Synthetic Construct

<400> SEQUENCE: 13

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Phe Gly Gln Gly Thr Lys Leu Glu Ile Lys
1               5                   10

<210> SEQ ID NO 15
<211> LENGTH: 122
<212> TYPE: PRT
<213> ORGANISM: Artificial Sequence
<220> FEATURE:
<223> OTHER INFORMATION: Synthetic Construct

<400> SEQUENCE: 15

Gln Val Gln Leu Val Gln Ser Gly Ala Glu Val Lys Asn Pro Gly Ser
1               5                   10                  15

Ser Val Arg Val Ser Cys Glu Ala Ser Gly Gly Thr Phe Ser Ser Phe
            20                  25                  30

Ala Ile Ser Trp Val Arg Gln Ala Pro Gly Gln Gly Leu Glu Trp Met
        35                  40                  45

Gly Arg Ile Ile Pro Ile Leu Asp Ile Val Lys Tyr Ala Gln Arg Phe
    50                  55                  60

Gln Gly Arg Val Thr Ile Ser Ala Asp Lys Ser Thr Ser Thr Ala Tyr
65                  70                  75                  80

Met Glu Leu Ser Ser Leu Arg Ser Glu Gly Thr Ala Val Tyr Tyr Cys
                85                  90                  95

Ala Arg Asp Asp Ile Ala Gly Ser Asp Phe Asp Ile Trp Gly Gln Gly
            100                 105                 110

Thr Met Val Thr Val Ser Ser Ala Ser Thr
        115                 120

<210> SEQ ID NO 16
<211> LENGTH: 107
<212> TYPE: PRT
<213> ORGANISM: Artificial Sequence
<220> FEATURE:
```

<223> OTHER INFORMATION: Synthetic Construct

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Thr Ser Tyr Pro Tyr
                85                  90                  95

Thr Phe Gly Gln Gly Thr Lys Leu Glu Ile Lys
            100                 105

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Gly Gly Ser Phe Ser Gly Tyr Ser Trp Ser
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Synthetic Construct

<400> SEQUENCE: 18

Glu Ile Tyr His Ser Gly Ser Thr Asn Tyr Asn Pro Ser Leu Lys Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic Construct

<400> SEQUENCE: 19

Ala Arg Glu Asn Leu Gln Gly Tyr Tyr Tyr Tyr Gly Met Asp Val
1               5                   10                  15

<210> SEQ ID NO 20
<211> LENGTH: 6
<212> TYPE: PRT
<213> ORGANISM: Artificial Sequence
<220> FEATURE:
<223> OTHER INFORMATION: Synthetic Construct

<400> SEQUENCE: 20

Gln Gly Ile Ser Ser Ser
1               5

<210> SEQ ID NO 21

```
<211> LENGTH: 3
<212> TYPE: PRT
<213> ORGANISM: Artificial Sequence
<220> FEATURE:
<223> OTHER INFORMATION: Synthetic Construct

<400> SEQUENCE: 21

Asp Ala Ser
1

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln Gln Phe Asn Ser Tyr Pro Arg Thr
1               5

<210> SEQ ID NO 23
<211> LENGTH: 25
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Gln Gln Trp Gly Ala Gly Leu Leu Lys Pro Ser Glu
1               5                   10                  15

Thr Leu Ser Leu Thr Cys Ala Val Tyr
            20                  25

<210> SEQ ID NO 24
<211> LENGTH: 14
<212> TYPE: PRT
<213> ORGANISM: Artificial Sequence
<220> FEATURE:
<223> OTHER INFORMATION: Synthetic Construct

<400> SEQUENCE: 24

Trp Ile Arg Gln Ser Pro Gly Lys Gly Leu Glu Trp Ile Gly
1               5                   10

<210> SEQ ID NO 25
<211> LENGTH: 30
<212> TYPE: PRT
<213> ORGANISM: Artificial Sequence
<220> FEATURE:
<223> OTHER INFORMATION: Synthetic Construct

<400> SEQUENCE: 25

Arg Val Thr Ile Ser Gly Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 26
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26
```

Trp Gly Gln Gly Thr Thr Val Thr Val Ser Ser Ala Ser Thr
1               5                   10

<210> SEQ ID NO 27
<211> LENGTH: 26
<212> TYPE: PRT
<213> ORGANISM: Artificial Sequence
<220> FEATURE:
<223> OTHER INFORMATION: Synthetic Construct

<400> SEQUENCE: 27

Ala Ile Gln Leu Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 28
<211> LENGTH: 17
<212> TYPE: PRT
<213> ORGANISM: Artificial Sequence
<220> FEATURE:
<223> OTHER INFORMATION: Synthetic Construct

<400> SEQUENCE: 28

Leu Ala Trp Tyr Gln Gln Lys Pro Gly Lys Ala Pro Lys Leu Leu Ile
1               5                   10                  15

Tyr

<210> SEQ ID NO 29
<211> LENGTH: 36
<212> TYPE: PRT
<213> ORGANISM: Artificial Sequence
<220> FEATURE:
<223> OTHER INFORMATION: Synthetic Construct

<400> SEQUENCE: 29

Ser Leu Glu Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Phe Gly Gln Gly Thr Lys Val Glu Ile Lys
1               5                   10

<210> SEQ ID NO 31
<211> LENGTH: 124
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Gln Gln Trp Gly Ala Gly Leu Leu Lys Pro Ser Glu
1               5                   10                  15

```
Thr Leu Ser Leu Thr Cys Ala Val Tyr Gly Gly Ser Phe Ser Gly Tyr
            20                  25                  30

Ser Trp Ser Trp Ile Arg Gln Ser Pro Gly Lys Gly Leu Glu Trp Ile
        35                  40                  45

Gly Glu Ile Tyr His Ser Gly Ser Thr Asn Tyr Asn Pro Ser Leu Lys
    50                  55                  60

Ser Arg Val Thr Ile Ser Gly Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Asn Leu Gln Gly Tyr Tyr Tyr Tyr Gly Met Asp Val Trp Gly
            100                 105                 110

Gln Gly Thr Thr Val Thr Val Ser Ser Ala Ser Thr
        115                 120
```

<210> SEQ ID NO 32
<211> LENGTH: 107
<212> TYPE: PRT
<213> ORGANISM: Artificial Sequence
<220> FEATURE:
<223> OTHER INFORMATION: Synthetic Construct

<400> SEQUENCE: 32

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys
            100                 105
```

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

```
Gly Gly Ser Phe Ser Ala Tyr Tyr Trp Ser
1               5                   10
```

<210> SEQ ID NO 34
<211> LENGTH: 16
<212> TYPE: PRT
<213> ORGANISM: Artificial Sequence
<220> FEATURE:
<223> OTHER INFORMATION: Synthetic Construct

<400> SEQUENCE: 34

```
Glu Ile Asn His Ser Gly Asn Thr Asn Tyr Asn Pro Ser Leu Glu Ser
1               5                   10                  15
```

```
<210> SEQ ID NO 35
<211> LENGTH: 11
<212> TYPE: PRT
<213> ORGANISM: Artificial Sequence
<220> FEATURE:
<223> OTHER INFORMATION: Synthetic Construct

<400> SEQUENCE: 35

Ala Arg Asn Trp Gly Pro Asn Ala Phe Asp Ile
1               5                   10

<210> SEQ ID NO 36
<211> LENGTH: 6
<212> TYPE: PRT
<213> ORGANISM: Artificial Sequence
<220> FEATURE:
<223> OTHER INFORMATION: Synthetic Construct

<400> SEQUENCE: 36

Gln Asp Ile Thr Ser Trp
1               5

<210> SEQ ID NO 37
<211> LENGTH: 3
<212> TYPE: PRT
<213> ORGANISM: Artificial Sequence
<220> FEATURE:
<223> OTHER INFORMATION: Synthetic Construct

<400> SEQUENCE: 37

Ala Ala Ser
1

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Gln Gln Ala Asn Ile Phe Pro Tyr Thr
1               5

<210> SEQ ID NO 39
<211> LENGTH: 25
<212> TYPE: PRT
<213> ORGANISM: Artificial Sequence
<220> FEATURE:
<223> OTHER INFORMATION: Synthetic Construct

<400> SEQUENCE: 39

Gln Val Gln Leu Gln Gln Trp Gly Ala Gly Leu Leu Lys Pro Ser Glu
1               5                   10                  15

Thr Leu Ser Leu Thr Cys Ala Val Tyr
            20                  25

<210> SEQ ID NO 40
<211> LENGTH: 14
<212> TYPE: PRT
<213> ORGANISM: Artificial Sequence
<220> FEATURE:
<223> OTHER INFORMATION: Synthetic Construct

<400> SEQUENCE: 40

Trp Ile Arg Gln Pro Pro Gly Lys Gly Leu Glu Trp Ile Gly
1               5                   10
```

```
<210> SEQ ID NO 41
<211> LENGTH: 30
<212> TYPE: PRT
<213> ORGANISM: Artificial Sequence
<220> FEATURE:
<223> OTHER INFORMATION: Synthetic Construct

<400> SEQUENCE: 41

Arg Val Thr Ile Ser Val Asp Thr Ser Lys Asn Gln Val Ser Leu Lys
1               5                   10                  15

Gln Ser Ser Val Thr Ala Ala Asp Thr Ala Val Tyr Tyr Cys
            20                  25                  30

<210> SEQ ID NO 42
<211> LENGTH: 14
<212> TYPE: PRT
<213> ORGANISM: Artificial Sequence
<220> FEATURE:
<223> OTHER INFORMATION: Synthetic Construct

<400> SEQUENCE: 42

Trp Gly Arg Gly Thr Met Val Thr Val Ser Ser Ala Ser Thr
1               5                   10

<210> SEQ ID NO 43
<211> LENGTH: 26
<212> TYPE: PRT
<213> ORGANISM: Artificial Sequence
<220> FEATURE:
<223> OTHER INFORMATION: Synthetic Construct

<400> SEQUENCE: 43

Asp Ile Gln Met Thr Gln Ser Pro Ser Ser Val Ser Ala Ser Val Gly
1               5                   10                  15

Asp Arg Val Thr Ile Thr Cys Arg Ala Ser
            20                  25

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Leu Val Trp Tyr Gln His Lys Pro Gly Lys Ala Pro Lys Leu Leu Ile
1               5                   10                  15

Tyr

<210> SEQ ID NO 45
<211> LENGTH: 36
<212> TYPE: PRT
<213> ORGANISM: Artificial Sequence
<220> FEATURE:
<223> OTHER INFORMATION: Synthetic Construct

<400> SEQUENCE: 45

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
            35
```

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Phe Gly Gln Gly Thr Lys Leu Glu Ile Lys
1               5                   10

<210> SEQ ID NO 47
<211> LENGTH: 120
<212> TYPE: PRT
<213> ORGANISM: Artificial Sequence
<220> FEATURE:
<223> OTHER INFORMATION: Synthetic Construct

<400> SEQUENCE: 47

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Ala Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Thr Asn Tyr Asn Pro Ser Leu Glu
    50                  55                  60

Ser Arg Val Thr Ile Ser Val Asp Thr Ser Lys Asn Gln Val Ser Leu
65                  70                  75                  80

Lys Gln Ser Ser Val Thr Ala Ala Asp Thr Ala Val Tyr Tyr Cys Ala
                85                  90                  95

Arg Asn Trp Gly Pro Asn Ala Phe Asp Ile Trp Gly Arg Gly Thr Met
            100                 105                 110

Val Thr Val Ser Ser Ala Ser Thr
        115                 120

<210> SEQ ID NO 48
<211> LENGTH: 107
<212> TYPE: PRT
<213> ORGANISM: Artificial Sequence
<220> FEATURE:
<223> OTHER INFORMATION: Synthetic Construct

<400> SEQUENCE: 48

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Thr Ser Trp
            20                  25                  30

Leu Val Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Tyr
                85                  90                  95

Thr Phe Gly Gln Gly Thr Lys Leu Glu Ile Lys
            100                 105